(12) United States Patent
Ridder et al.

(10) Patent No.: US 9,528,159 B2
(45) Date of Patent: *Dec. 27, 2016

(54) METHOD FOR IMPROVED DIAGNOSIS OF DYSPLASIAS

(71) Applicant: Ventana Medical Systems, Inc., Tuscon, AZ (US)

(72) Inventors: Ruediger Ridder, Schriesheim (DE); Anja Reichert, Nussloch (DE); Marcus Trunk, Heidelberg (DE); Richard Batrla, Heidelberg (DE)

(73) Assignee: VENTANA MEDICAL SYSTEMS, INC., Tucson, AZ (US)

(*) Notice: Subject to any disclaimer, the term of this patent is extended or adjusted under 35 U.S.C. 154(b) by 321 days.

This patent is subject to a terminal disclaimer.

(21) Appl. No.: 13/798,998

(22) Filed: Mar. 13, 2013

(65) Prior Publication Data

US 2013/0189685 A1   Jul. 25, 2013

Related U.S. Application Data

(62) Division of application No. 12/289,487, filed on Oct. 29, 2008, now Pat. No. 8,975,036, which is a division of application No. 10/533,384, filed as application No. PCT/EP03/50738 on Oct. 21, 2003, now abandoned.

(30) Foreign Application Priority Data

Oct. 28, 2002 (EP) .................................. 02024030
Mar. 7, 2003 (EP) .................................. 03100584

(51) Int. Cl.
G01N 33/574 (2006.01)
C12Q 1/68 (2006.01)

(52) U.S. Cl.
CPC .......... *C12Q 1/6886* (2013.01); *G01N 33/574* (2013.01); *G01N 33/57411* (2013.01); *G01N 33/57484* (2013.01)

(58) Field of Classification Search
CPC .................................................. G01N 33/574
USPC ................... 436/64, 501; 435/4, 7.23
See application file for complete search history.

(56) References Cited

U.S. PATENT DOCUMENTS

| | | | |
|---|---|---|---|
| 4,281,061 A | 7/1981 | Zuk et al. | |
| 5,723,313 A | 3/1998 | Sherr et al. | |
| 5,876,965 A | 3/1999 | Sherr et al. | |
| 6,033,847 A | 3/2000 | Sherr et al. | |
| 6,172,194 B1 | 1/2001 | Sherr et al. | |
| 6,303,323 B1 | 10/2001 | Laskey et al. | |
| 6,316,208 B1 | 11/2001 | Roberts et al. | |
| 6,407,062 B1 | 6/2002 | Sherr et al. | |
| 6,482,929 B1 | 11/2002 | Sherr et al. | |
| 6,709,832 B1 | 3/2004 | von Knebel Doeberitz | |
| 6,939,670 B2 | 9/2005 | Pressman et al. | |
| 7,361,460 B2 | 4/2008 | Williams et al. | |
| 7,422,859 B2 | 9/2008 | Ridder et al. | |
| 7,452,727 B2 | 11/2008 | Henning et al. | |
| 7,517,662 B2 | 4/2009 | Ridder et al. | |
| 8,277,190 B2 | 10/2012 | Piersall et al. | |
| 8,728,745 B2 | 5/2014 | Martin et al. | |
| 2002/0106685 A1 | 8/2002 | Henning et al. | |
| 2003/0143646 A1 | 7/2003 | Laskey et al. | |
| 2003/0157482 A1 | 8/2003 | Keesee et al. | |
| 2007/0243552 A1 | 10/2007 | Williams et al. | |

FOREIGN PATENT DOCUMENTS

| | | |
|---|---|---|
| EP | 0853681 A1 | 7/1998 |
| EP | 1025444 A1 | 8/2000 |
| EP | 1 217 377 B1 | 6/2002 |
| EP | 1 387 173 A | 2/2004 |
| WO | WO 97 12060 | 4/1997 |
| WO | WO 9921014 A1 | 4/1999 |
| WO | WO 00 01845 A2 | 1/2000 |
| WO | WO 01 40300 A | 6/2001 |
| WO | WO 02 08764 A | 1/2002 |
| WO | WO 02 08764 A1 | 1/2002 |
| WO | WO 2004 013631 A2 | 2/2004 |

OTHER PUBLICATIONS

Wharton et al. (Neuropathol. Appl. Neurobiol. Aug. 2001; 27 (4): 305-13).*

Agoff, et al.; "p16$^{INK4a}$ Expression Correlates with Degree of Cervical Neoplasia: A Comparison with Ki-67 Expression and Detection of High-Risk HPV Types"; Mod. Pathol.; vol. 16, No. 7, pp. 665-673 (Jul. 2003).

Aslani, et al.; "Evaluation of Ki67, p16 and CK17 Markers in Differentiating Cervical Intraepithelial Neoplasia and Benign Lesions"; Iran J Med Sci; vol. 38, No. 1, pp. 15-21 (Mar. 2013).

(Continued)

*Primary Examiner* — Stephen Rawlings

(74) *Attorney, Agent, or Firm* — Perkins Coie LLP; Viola T. Kung

(57) ABSTRACT

The present invention relates to a method for improved diagnosis of dysplasias based on simultaneous detection of INK4a gene products and at least one marker for cell proliferation. Particularly the present invention provides a method for discriminating dysplastic cells over-expressing INK4a gene products from cells over-expressing INK4a gene products without being dysplastic by detection of a marker suitable for characterizing the proliferation properties of the respective cell. The characterization of the proliferation properties may comprise the detection of a marker or a set of markers characteristic for active cell proliferation and/or a marker or a set of markers characteristic for retarded or ceased cell proliferation. The method presented herein thus enables for a specific diagnosis of dysplasias in histological and cytological specimens.

3 Claims, 8 Drawing Sheets

(8 of 8 Drawing Sheet(s) Filed in Color)

(56) References Cited

OTHER PUBLICATIONS

Duggan, et al.; "Atypical immature cervical metaplasia: immunoprofiling and longitudinal outcome"; Hum. Pathol.; vol. 37, No. 11, pp. 1473-1481 (Nov. 2006).

Iaconis, et al; "p16 and Ki-67 Immunostaining in Atypical Immature Squamous Metaplasia of the Uterine Cervix"; Arch Pathol Lab Med; vol. 131, No. 9, pp. 1343-1349 (Sep. 2007).

Ikenberg, et al.; "Screening for Cervical Cancer Precursors With p16/Ki-67 Dual-Stained Cytology: Results of the PALMS Study"; J. Natl. Cancer Inst.; vol. 105, No. 20, pp. 1550-1557 (Oct. 4, 2013).

Ma, et al.; "A Newly Recognized Variant of Cervical Squamous Intraepithelial Neoplasia"; Am. J. Surg. Pathol; No. 28, No. 11, pp. 1474-1484 (Nov. 2004).

Petry, et al.; "Triaging Pap cytology negative, HPV positive cervical cancer screening results with p16/Ki-67 Dual-stained cytology"; Gynecologic Oncology; vol. 121, No. 3, pp. 505-509 (Jun. 1, 2011).

Portari, et al.; "Immunohistochemical Expression of Cyclin D1, $p16^{Ink4a}$, $p21^{WAF1}$, and Ki-67 Correlates With the Severity of Cervical Neoplasia"; Int. J. Gynecol. Pathol.; vol. 32, No. 5, pp. 501-508 (Sep. 2013).

Ressler, et al.; "$p16^{INK4A}$ is a robust in vivo biomarker of cellular aging in human skin"; Aging Cell.; vol. 5, No. 5, pp. 379-389 (Oct. 2006).

Samarawardana, et al.; "Dual Stain Immunohistochemical Localization of $p16^{INK4A}$ and ki-67: A Synergistic Approach to Identify Clinically Significant Cervical Mucosal Lesions"; Appl. Immunohistochem. Mol. Morphol.; vol. 19, No. 6, pp. 514-518 (Dec. 2011).

Schmidt, et al.; "p16/Ki-67 Dual-Stain Cytology in the Triage of ASCUS and LSIL Papanicolaou Cytology"; Cancer Cytopathology; vol. 119, No. 3, pp. 158-166 (Jun. 25, 2011).

Singh, et al.; "Immunocytochemical Colocalization of $P16^{INK4a}$ and Ki-67 Predicts CIN2/3 and AIS/Adenocarcinoma"; Cancer Cytopathol.; vol. 120, No. 1, pp. 26-34 (Feb. 25, 2012).

Zappacosta, et al.; "Chromogenic In Situ Hybridization and p16/Ki67 Dual Staining on Formalin-Fixed Paraffin-Embedded Cervical Specimens: Correlation with HPV-DNA Test, E6-E7 mRNA Test, and Potential Clinical Applications"; BioMed Research International; pp. 1-11 (2013).

Burgess et al.; "Two-colour immunoenzymatic technique using sequential staining by APAAP to evaluate two cell antigens"; Journal of Clinical Pathology; vol. 45, No. 3, pp. 206-209 (Mar. 1992).

Cohen et al.; "Identification of cell subpopulations by dual-color surface immunofluorescence using biotinylated and unlabeled monoclonal antibodies"; Cytometry; vol. 9, No. 4, pp. 303-308 (Jul. 1988).

Goodwin et al.; "Rapid Induction of Senescence in Human Cervical Carcinoma Cells"; Proc. Natl. Acad. Sci. USA; vol. 97, No. 20, pp. 10978-10983 (Sep. 26, 2000).

Hilgarth; "Clarification of Cytologically Doubtful Findings"; Fortschr. Med.; vol. 94, No. 27, pp. 1485-1487 (Sep. 23, 1976).

Jakobsen et al.; "Flow cytometric classification of biopsy specimens from cervical intraepithelial neoplasia"; Cytometry; vol. 4, No. 2, pp. 166-169 (Sep. 1983).

Keating et al.; "Surrogate biomarkers of HPV infection in cervical neoplasia screening and diagnosis"; Advances in Anatomic Pathology; vol. 8, No. 2, pp. 83-92 (Mar. 2001).

Sano et al.; "Expression status of p16 protein is associated with human papillomavirus oncogenic potential in cervical and genital lesions"; American Journal of Pathology; vol. 153, No. 6, pp. 1741-1748 (Dec. 1998).

Schmidt et al.; "Proliferation Marker pKi-67 Occurs in Different Isoforms With Various Cellular Effects"; Journal of Cellular Biochemistry; vol. 91, pp. 1280-1292 (2004).

Smedts et al.; "Changing Patterns of Keratin Expression During Progression of Cervical Intraepithelial Neoplasia"; American Journal of Pathology; vol. 136, No. 3, pp. 657-668 (Mar. 1990).

Van Agthoven et al.; "Differential Expression of Estrogen, Progesterone, and Epidermal Growth Factor Receptors in Normal, Benign, and Malignant Human Breast Tissues using Dual Staining Immunohistochemistry"; American Journal of Pathology; vol. 144, No. 6, pp. 1238-1246 (Jun. 1994).

Benassi et al., *Involvement of INK4A Gene Products in the Pathogenesis and Development of Human Osteosarcoma*, 92(12) Cancer 3062-3067 (2001).

Kourea et al., *Deletions of the INK4A Gene Occur in Malignant Peripheral Nerve Sheath Tumors but not in Neurofibromas*, 155(6) American Journal of Pathology 1855-1860 (Dec. 1999).

Lu et al. (1999) Abnormal Expression of Sex Steroid Receptors and Cell Cycle-Related Molecules in Adenocarcinoma in Situ of the Uterine Cervix, Int. J. Gynecol. Pathol., 18:109-14.

Park et al. (1999) Detection of p16 gene alteration in cervical cancer using tissue microdissection and LOH study, Cancer Lett., 136:101-08.

Cameron et al. (2002) Immunohistochemical staining with MIB1, bd2 and p16 assists in the distinction of cervical glandular intraepithelial neoplasia from tubo-endometrial metaplasia, endometriosis and microglandular hyperplasia, Histopathology 41:313-21.

Bullwinkel et al., "Ki-67 Protein is Associated with Ribosomal RNA Transcription in Quiescent and Proliferating Cells," *J. Cell Physiol.*, vol. 206, No. 3, 624-635 (2006).

Martin et al., "Expression of p16/INK4a in Posttransplantation Lymphoproliferative Disorders," *Am. J. Pathol.*, vol. 156, No. 5, 1573-1579 (2000).

Dai et al., "$p16^{INK4a}$ Expression Begins Early in Human Colon Neoplasia and Correlates Inversely with Markers of Cell Proliferation," Gastroenterology, vol. 119, No. 4, 929-942 (2000).

Emig et al., "Aberrant Cytoplasmic Expression of the p16 Protein in Breast Cancer is Associated with Accelerated Tumour Proliferation," *Br. J. Cancer.*, vol. 78, No. 11, 1661-1668 (1998).

He et al., "Expression, Deletion and Mutation of p16 Gene in Human Gastric Cancer," *World J. Gastroenterol.*, vol. 7, No. 4, 515-521 (2001).

Myung et al., "Loss of p16 and p27 is Associated with Progression of Human Gastric Cancer," *Cancer Lett.*, vol. 153, 129-136 (2000).

Nakao et al., "Induction of p16 During Immortalization by HPV 16 and 18 and Not During Malignant Transformation," *Br. J. Cancer*, vol. 75, No. 10, 1410-1416 (1997).

O'Nions et al., "p73 is Over-Expressed in Vulval Cancer Principally as the Δ2 Isoform," *Br. J. Cancer*, vol. 85, No. 10, 1551-1556 (2001).

Sano et al., "Overexpression of P16 and P14ARF is Associated with Human Papillomavirus Infection in Cervical Squamous Cell Carcinoma and Dysplasia," *Pathol. Int.*, vol. 52, 375-383 (2002).

Sano et al., "Expression Status of p16 Protein is Associated with Human Papillomavirus Oncogenic Potential in Cervical and Genital Lesions," *Am. J. Pathol.*, vol. 153, No. 6, 1741-1748 (1998).

Sherr, "The Ink4a/Arf Network in Tumor Suppression," *Nature Rev. Mol. Cell. Biol.*, vol. 2, 731-737 (2001).

Takeuchi et al., "Altered p16/MTSi/CDKN2 and Cycling D1/PRAD-1 Gene Expression is Associated with the Prognosis of Squamous Cell Carcinoma of the Esophagus," *Clin. Cancer Res.*, vol. 3, 2229-2236 (1997).

Tsujie et al., "Expression of Tumor Suppressor Gene p16INK4 Products in Primary Gastric Cancer" Oncology, vol. 58, 126-136 (2000).

Bepler et al., "Mcm2: A Novel Diagnostic Marker for Early Detection of Premalignant Lesions of the Lung," *Proceedings of the American Association for Cancer Research Annual*, vol. 42, 356 (2001).

Klaes et al., "Overexpression of p16(INK4a) as a Specific Marker for Dysplastic and Neoplastic Epithelial Cells of the Cervix Uteri," *Int. J. Cancer*, vol. 92, No. 2, 276-284 (2001).

Ridder et al., "Novel Biomarkers for HPV Associated Lesions," *Gynäkologe*, vol. 36, No. 4, 323-330 (2003).

Riethdorf Lutz et al., "Human Papillomaviruses, Expression of p16INK4a, and Early Endocervical Granular Neoplasia," *Hum. Pathol.*, vol. 33, No. 9, 899-904 (2002).

(56) References Cited

OTHER PUBLICATIONS

Sanchez-Aguilera et al., "p14(ARF) Nuclear Overexpression in Aggressive B-cell Lymphomas is a Sensor of Malfunction of the Common Tumor Suppressor Pathways," *Blood*, vol. 99, No. 4, 1411-1418 (2002).
Simonart et al., "Antiproliferative and Apoptotic Effects of Iron Chelators on Human Cervical Carcinoma Cells," *Gynecol. Oncol.*, vol. 85, No. 1, 95-102 (2002).
Von Knebel et al., "New Markers to Identify HPV-Transformed Dysplastic Cervical Epithelia," *Acta Cytol.*, vol. 46, No. 1, Supplement, 156 (2002).
Klaes et al., "p16INK4a Immunohistochemistry Improves Interobserver Agreement in the Diagnosis of Cervical Intraepithelial Neoplasia," *Am. J. Surg. Pathol.*, vol. 26, No. 11, 1389-1399 (2002).
Keating et al., "Ki-67, Cyclin E, and p16$^{INK4}$ are Complimentary Surrogate Biomakers for Human Papilloma Virus-Related Cervical Neoplasia," *Am. J. Surg. Pathol.*, 25, No. 7, 884-891 (2001).
Wright et al., "2006 Consensus Guidelines for the Management of Women with Abnormal Cervical Cancer Screening Test," *Am. J. Obstet. Gynecol.*, 346-355 (Oct. 2007).
Parker et al. (1997) "Molecular Characterization of Adenocarcinoma of the Cervix," *Gynecol. Oncol.* 64:242-51.
Guccione et al. (2002) "Comparative Analysis of the Intracellular Location of the High- and Low-Risk Human Papillomavirus Oncoproteins," *Virology* 293:20-25.
Solomon et al. (2001) "Comparison of Three Management Strategies for Patients With Atypical Squamous Cells of Undetermined Significance: Baseline Results From a Randomized Trial," *J. Natl. Cancer Inst.* 93(4):293-99.
Tockman et al. (1992) "Considerations in Bringing a Cancer Biomarker to Clinical Application," *Cancer Res.* (Suppl.) 52:2711s-18s.
von Knebel Doeberitz (2001) "New Molecular Tools for Efficient Screening of Cervical Cancer," *Dis. Markers* 17(3):123-28 (Abstract Only).
Khan et al. (1993) "Inhibition of Growth, Transformation, and Expression of Human Papillomavirus Type 16 E7 in Human Keratinocytes by Alpha Interferons," *J. Virol.* 67(6): 3396-403.
Brown et al. (1988) "Carcinoma of the cervix uteri: An assessment of tumour proliferation using the monoclonal antibody Ki67," *Br. J. Cancer* 57(2):178-81.
Barnard et al. (1987) "Proliferative index in breast carcinoma determined in situ by Ki67 immunostaining and its relationship to clinical and pathological variables," *J. Pathol.* 152(4):287-95.
Kubbutat et al. (1994) "Epitope analysis of antibodies recognising the cell proliferation associated nuclear antigen previously defined by the antibody Ki-67 (Ki-67 protein)," *J. Clin. Pathol.* 47:524-28.
Ross and Hall (1995) "Ki67: from antibody to molecule to understanding?" *J. Clin. Pathol.: Mol. Pathol.* 48:M113-17.
Schluter et al. (1993) "The Cell Proliferation-associated Antigen of Antibody Ki-67: A Very Large, Ubiquitous Nuclear Protein with Numerous Repeated Elements, Representing a New Kind of Cell Cycle-maintaining Proteins," *J. Cell. Bio.* 123:513-22.
Duchrow et al. (1996) "Molecular Characterization of the gene locus of the human cell proliferation-associated nuclear protein defined by monoclonal antibody Ki-67," *Cell. Prolif.* 29:1-12.
Scholzen and Gerdes (2000) "The Ki-67 protein: From the known and the unknown," *J. Cell Physiol.* 182:311-22.
Buskens et al., Digestive Disease Week Abstracts and Itinerary Planner, 2003, abstract No:850; See also "Adenocarcinomas of the gastro-esophageal junction: A comparative study of the gastric cardia and the esophagus with respect to cyclooxygenase-2 expression" *Gastroenterol.* 124(4) Suppl. 1: A117-18.
Riethdorf et al. (2001) "Analysis of p16/MTS1, Ki67 and HPV 16/18 E6/E7 oncogene transcription in adenocarcinoma in situ and benign glandular lesions of the cervix uteri," *Virchows Archiv.* 439(3):338 (Abstract).
Midle-Langosch et al. (2001) "Expression of cyclin-dependent kinase inhibitors p16$^{MTS1}$, p21$^{WAF1}$, and p27$^{KIP1}$ in HPV-positive and HPV-negative cervical adenocarcinomas," *Virchows Archiv.* 439(1):55-61.
Konno et al. (1992) "Detection of human papillomavirus DNA in normal epithelium and in squamous metaplasia of the uterine cervix by the polymerase chain reaction," *Tohoku J. Exp. Med.* 168(3):491-97.
Choo et al. (1987) "Integration of human papillomavirus type 16 into cellular DNA of cervical carcinoma: Preferential deletion of the E2 gene and invariable retention of the long control region and the E6/E7 open reading frames," *Virology* 161(1):259-61 (Abstract only).
Nindl et al. (1997) "Human papillomavirus distribution in cervical tissues of different morphology as determined by hybrid capture assay and PCR," *Inter. J. Gynecol. Pathol.* 16(3):197-204.
Wiest et al. (2002) "Involvement of intact HPV16 E6/E7 gene expression in head and neck cancers with unaltered p53 status and perturbed pRb cell cycle control," *Oncogene* 21(10):1510-17.
Sdek et al. (2002) "Influence of HPV16 on expression of Rb, p16 and cyclin D1 in oral epithelial cell," *Chinese J. Stomatol.* 37(2):84-86.

\* cited by examiner

METHOD FOR IMPROVED DIAGNOSIS OF DYSPLASIAS

This application is a continuation application of U.S. patent application Ser. No. 12/289,487, filed on Oct. 29, 2008, now U.S. Pat. No. 8,975,036, which is a divisional application of U.S. patent application Ser. No. 10/533,384, filed on Jun. 8, 2006, which is a National Stage of International Application PCT/EP03/050738, filed Oct. 21, 2003, published in English as WO 2004/038418 on May 6, 2004, which claims the priority of EP 02024030.5 filed on Oct. 28, 2002; and EP 03100584.6 filed on Mar. 7, 2003.

FIELD OF THE INVENTION

The present invention relates to a method for improved diagnosis of dysplasias based on simultaneous detection of INK4a gene products and at least one marker for cell proliferation. In particular, the present invention provides a method for discriminating dysplastic cells over-expressing INK4a gene products from cells over-expressing INK4a gene products without being dysplastic by detection of a marker suitable for characterising the proliferation properties of the respective cell. The characterisation of the proliferation properties may comprise the detection of a marker or a set of markers characteristic for active cell proliferation and/or a marker or a set of markers characteristic for retarded or ceased cell proliferation. The method presented herein thus enables a specific diagnosis of dysplasias in histological and cytological specimens.

The detection of the over-expression of $p16^{INK4a}$ in biological samples has proven as a useful marker in the detection of anogenital lesions, such as carcinoma of the uterine cervix (see WO00/01845; Klaes et al., Int. J. Cancer: 92, 276-284 (2001)). The method based on $p16^{INK4a}$-specific immuno-chemical staining allows for a sensitive and specific identification of dysplastic cells in tissue sections and in cytological samples.

In immuno-histochemical examinations of tissues, dysplastic and neoplastic cells can be stained using a $p16^{INK4a}$ specific antibody mediated staining procedure. The histological diagnosis of neoplastic lesions can thus be supported by a staining procedure based on a molecular marker characteristic for transformation of cells in anogenital lesions. The diagnosis, whether or not cells are neoplastic, in these procedures is not solely based on the $p16^{INK4a}$ specific staining, but does also rely on the histological information.

This is due to the fact that, in about 20-30% of samples, metaplastic cells show some immunoreactivity with $p16^{INK4a}$ specific antibodies, and thus are stained in the course of the procedures. Yet the staining pattern of these metaplastic cells differs from the pattern of neoplastic lesions. Metaplastic cells give rise to a patchy or focal staining pattern, whereas neoplastic lesions give rise to diffuse staining pattern. Moreover, the staining intensities of metaplastic cells are predominantly less than that of neoplastic cells.

The common methods used in screening tests for the early detection of dysplasias and/or neoplasias do not employ histology based tests, but rather rely on cytological testing procedures. Yet especially in cases when there is no histological information available concerning the architecture of tissues, such as, for example, in cytological examinations, testing for $p16^{INK4a}$ over-expression alone may lead to false positive results. This is due to the fact that those fractions of metaplastic cells expressing $p16^{INK4a}$ at detectably elevated levels may not be differentiated by means of a histologic criteria.

The percentage of cells showing over-expression of $p16^{INK4a}$ increases in the course of emergence of dysplasias. So, in neoplastic or pre-neoplastic stages, when only a restricted population of neoplastic or pre-neoplastic cells is present in samples, the immunoreactivity of $p16^{INK4a}$ may be weak. This weak immunoreactivity may be of about the level as the level caused by metaplastic cells. In later stages of dysplasias, the overall immunoreactivity of $p16^{INK4a}$ is stronger, so neoplastic lesions are easily discernible from metaplasias even in a cytological testing format. This might lead to cases where the presence of metaplastic cells expressing $p16^{INK4a}$ might be confused with the presence of neoplastic cells, and thus produce a false positive result.

Especially in screening tests, where the detection of early stages of neoplasias is desirable, this condition is quite unpleasant. This is especially true, as the $p16^{INK4a}$ based diagnosis has proven to be a valuable tool in histological examinations and the application in cytological based screening procedures would be able to enhance these established procedures.

To reduce false positive results in cytological testing formats and thereby further enhance the fidelity of the $p16^{INK4a}$ mediated diagnosis of anogenital lesions, a method for discriminating the metaplasias from neoplastic and dysplastic lesions would be desirable. A method for the discrimination of metaplasias from neoplastic and pre-neoplastic lesions is provided within the embodiments claimed according to the present invention.

For supporting the discrimination of metaplasias from neoplastic lesions in testing procedures based on the over-expression of $p16^{INK4a}$, a marker molecule would be desirable that is expressed in neoplastic and/or pre-neoplastic cells and tissues and which is not expressed simultaneously with INK4a gene products in one single metaplastic cell.

A solution to the problem present in the art is provided by the methods claimed according to this invention. In the course of the experiments leading to the present invention, the inventors have found that a combination of detection of the presence or absence and/or the level of $p16^{INK4a}$, in combination with at least one marker for cell proliferation, such as e.g. Ki67, Ki-S2, mcm5 or mcm2, may solve the problem present in the art.

In the art, a couple of documents pertaining to the use of a combination of molecular markers for improved diagnosis of dysplasias is presented. In WO0208764, a method for improved diagnosis of cervical malignancies is disclosed using a combination of an HPV marker and a marker for cell proliferation or viral activity. $p16^{INK4a}$ is mentioned in the context of this invention as a viral activity marker to be combined with HPV markers.

In EP1217377, a method for automated detection of cervical malignancies is disclosed that is mediated by detection of more than one marker molecule. Some defined marker combinations are named within the document. There is no disclosure in this document relating to the choice of suitable markers for a combination. The purpose of the combination in this application is improved fidelity of the automated analysis of staining patterns in biological cytological specimens. This document mentions combination of $p16^{INK4a}$ with other tumor markers.

WO02059616 discloses a method for detection of cell-cycle disturbances for improved diagnosis of cervical malignancies. The document discloses that dysplastic cells exhibit disturbances in cell cycle control, and may thus be identified by means of detection of cyclin E type proteins together with post G1 substances in cells.

Jeffrey Keating in "Ki67, Cyclin E, and p16$^{INK4a}$ Are Complimentary Surrogate Biomarkers for human papilloma Virus-Related Cervical Neoplasia" (American Journal of Surgical Pathology 25(7): 884-891, (2001)) discloses the complementarity of the use of p16$^{INK4a}$, Ki67, and Cyclin E in the course of diagnosis of cervical dysplasias. The document refers to the problems of each single marker in the detection of dysplasias, and states that p16$^{INK4a}$ in combination with Cyclin E may be suitable to overcome the drawbacks of the single marker molecule, especially when cytological specimens are under examination. No disclosure teaching use of p16$^{INK4a}$ in concert with a marker characteristic of proliferating cells such as Ki67 is given. The document does not teach the combination of p16$^{INK4a}$ for use in diagnostic methods; moreover, the disclosure pertains to a restricted use of Ki67 in cervical differential diagnosis, and thus, teaches away from the use of this marker in diagnosis of cervical malignancies.

In the art, there is no disclosure teaching the use of a combination of p16$^{INK4a}$ with a marker characteristic of cell proliferation for use in a diagnostic method for improved discrimination of p16$^{INK4a}$ positive non-dysplastic cells from p16$^{INK4a}$ positive dysplasias. WO02059616 does not give a hint as to the use of p16$^{INK4a}$ in the detection of dysplastic cell proliferation. EP1217377 does not teach a purpose for the combination of tumor markers in the course of the detection other than the automation of the analysis process. There is no disclosure pertaining to the advantage of combinations for specific discrimination purposes such as discrimination of dysplastic cells from e.g. metaplastic cells in cervical specimens.

SUMMARY OF THE INVENTION

The inventors of the present invention sought to overcome the drawback present in the art that p16$^{INK4a}$, over-expressed in various dysplasias, may also be detected in some other non-dysplastic cells. The discrimination between non-dysplastic p16$^{INK4a}$ positive cells and dysplastic cells over-expressing p16$^{INK4a}$ may be based on the proliferation characteristics of the respective cells. In normal cells, p16$^{INK4a}$ inhibits cdk4, and thus inhibits proliferation. In contrast, in dysplastic cells, this regulation is impaired. Thus, p16$^{INK4a}$ does not lead—despite its uncommonly high expression level—to an inhibition of the cell proliferation.

The inventors of the present invention found that dysplastic cells may be discriminated from cells exhibiting controlled cell proliferation by the simultaneous detection of p16$^{INK4a}$ with a marker characteristic for cell proliferation. Due to the fact that, in normal cells, elevated levels of p16$^{INK4a}$ inhibit cell proliferation, cells over-expressing p16$^{INK4a}$ may be classified as being dysplastic provided they are exhibiting the characteristics of active cell proliferation.

BRIEF DESCRIPTION OF THE DRAWINGS

The patent or application file contains at least one drawing executed in color. Copies of this patent or patent application publication with drawing(s) will be provided by the Office upon request and payment of the necessary fee.

FIG. 1 shows staining of a severe dysplasia using antibodies directed against p16$^{INK4a}$. For experimental details, see Example 1. Immunoreactivity for p16$^{INK4a}$ renders green fluorescence. Almost all cells of the lesion are diffusely positively stained in the cytoplasm and in the nuclei.

FIG. 2 shows staining of a severe dysplasia using antibodies directed against Ki67. For experimental details, see Example 1. Immunoreactivity for Ki67 renders red fluorescence. Many cells of the dysplasia show nuclear positivity for Ki67.

FIG. 3 shows staining of a severe dysplasia using antibodies directed against Ki67 and those directed against p16$^{INK4a}$. For experimental details, see Example 1. Immunoreactivity for Ki67 renders red fluorescence, immunoreactivity for p16$^{INK4a}$ renders green fluorescence and the overlay of red and green fluorescence renders yellow fluorescence. Many cells of the dysplasia show nuclear positivity for Ki67, as well as positivity for p16$^{INK4a}$, and thus give rise to yellow fluorescence.

FIG. 4 shows staining of a squamous metaplasia using antibodies directed against p16$^{INK4a}$. For experimental details, see Example 1. Immunoreactivity for p16$^{INK4a}$ renders green fluorescence. Some cells of the metaplasia stain diffusely positive in the cytoplasm and in the nuclei.

FIG. 5 shows staining of a squamous metaplasia using antibodies directed against Ki67. For experimental details, see Example 1. Immunoreactivity for Ki67 renders red fluorescence. Many cells of the squamous metaplasia show nuclear positivity for Ki67. Areas that have been identified as positively expressing p16$^{INK4a}$ do not show any positive staining for Ki67, indicating lack of expression of the antigen in these areas.

FIG. 6 shows staining of a squamous metaplasia using antibodies directed against Ki67 and against p16$^{INK4a}$. For experimental details, see Example 1. Immunoreactivity for Ki67 renders red fluorescence, immunoreactivity for p16$^{INK4a}$ renders green fluorescence and the overlay of red and green fluorescence renders yellow fluorescence. Areas that are positively expressing p16$^{INK4a}$ do not show any positive staining for Ki67, indicating lack of expression of the antigen in these areas. No cells in the specimen give rise to yellow fluorescence.

FIG. 7 shows staining of a severe dysplasia using antibodies directed against Ki67 and against p16$^{INK4a}$. For experimental details, see Example 6. Immunoreactivity for Ki67 renders red nuclear staining, immunoreactivity for p16$^{INK4a}$ renders brownish staining over the whole cell, and double staining renders brown cells with red nuclei. Many cells of the dysplasia show nuclear positivity for Ki67, as well as positivity for p16$^{INK4a}$, and thus, give rise to a pattern of brown cells with red nuclei.

FIG. 8 shows staining of a severe dysplasia using antibodies directed against Ki67 and against p16$^{INK4a}$. For experimental details, see Example 7. Immunoreactivity for Ki67 renders red nuclear staining, immunoreactivity for p16$^{INK4a}$ renders brownish staining over the whole cell, and double staining renders brown cells with red nuclei. Many cells of the dysplasia show nuclear positivity for Ki67 as well as positivity for p16$^{INK4a}$, and thus, give rise to a pattern of brown cells with red nuclei.

DETAILED DESCRIPTION OF THE INVENTION

Figure 1:
FIG. 1 is an example of fluorescent staining of a histological specimen of the cervix uteri.
Figure 2:
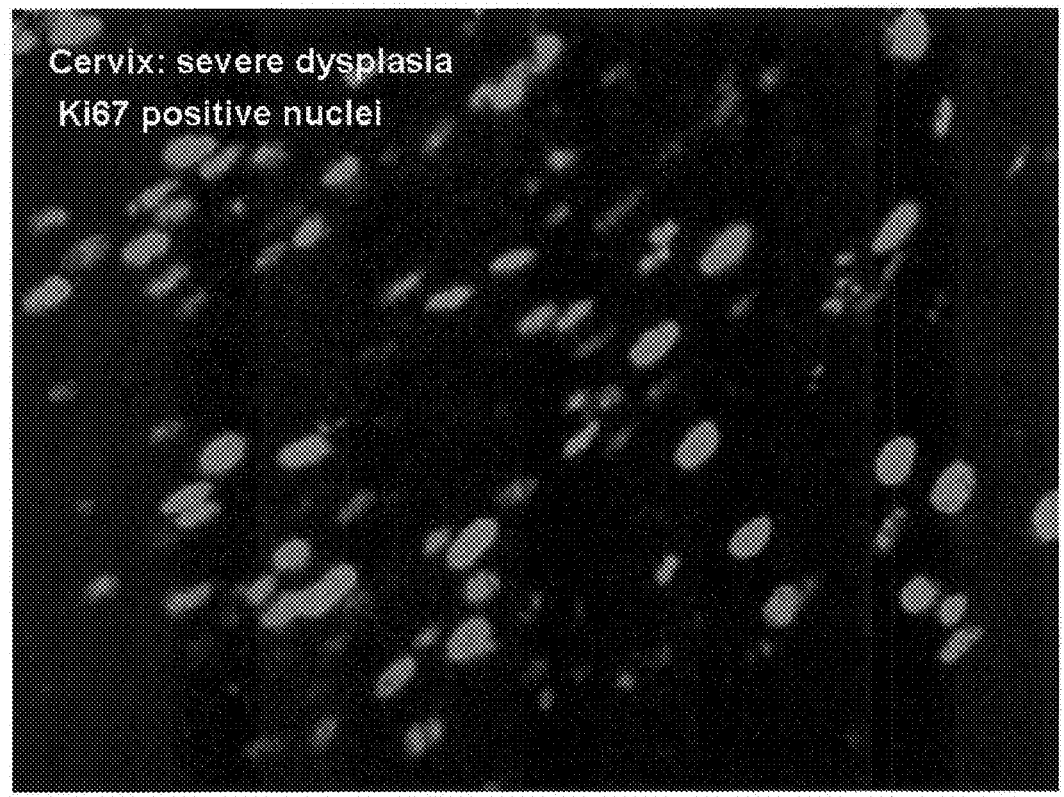
FIG. 2 is an example of fluorescent staining of a histological specimen of the cervix uteri.
Figure 3:
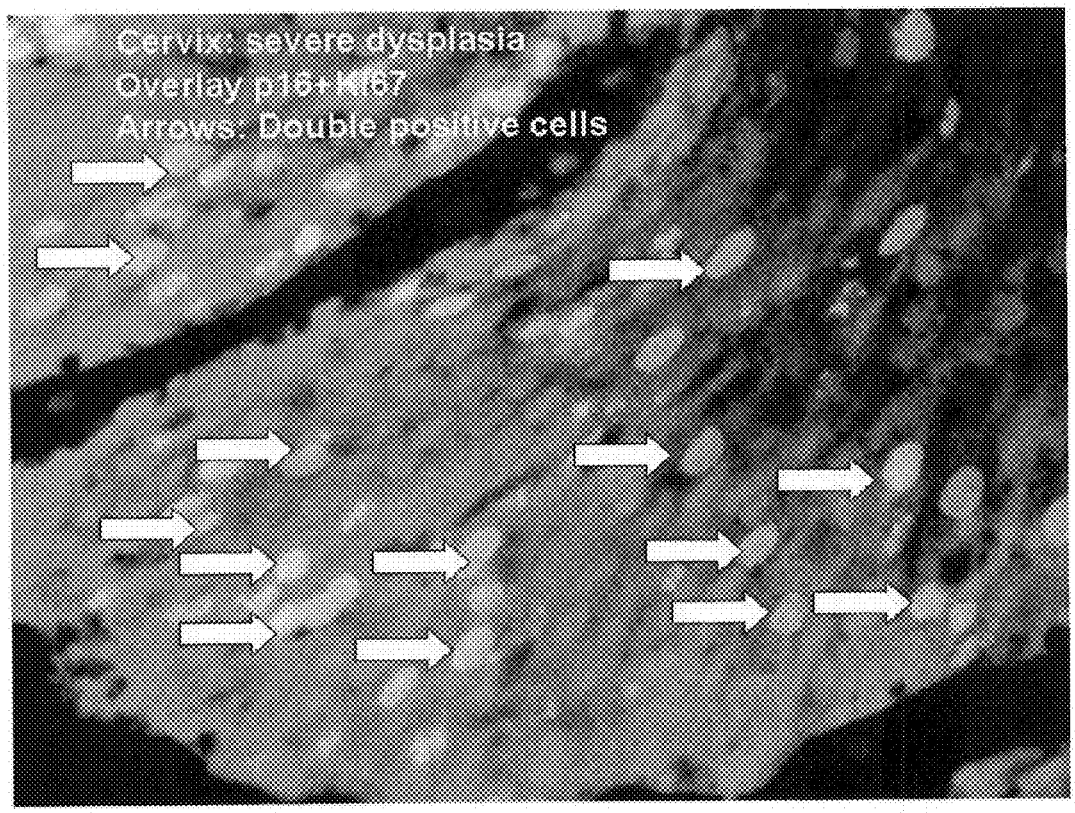
FIG. 3 is an example of fluorescent double staining of a histological specimen of the cervix uteri.
Figure 4:
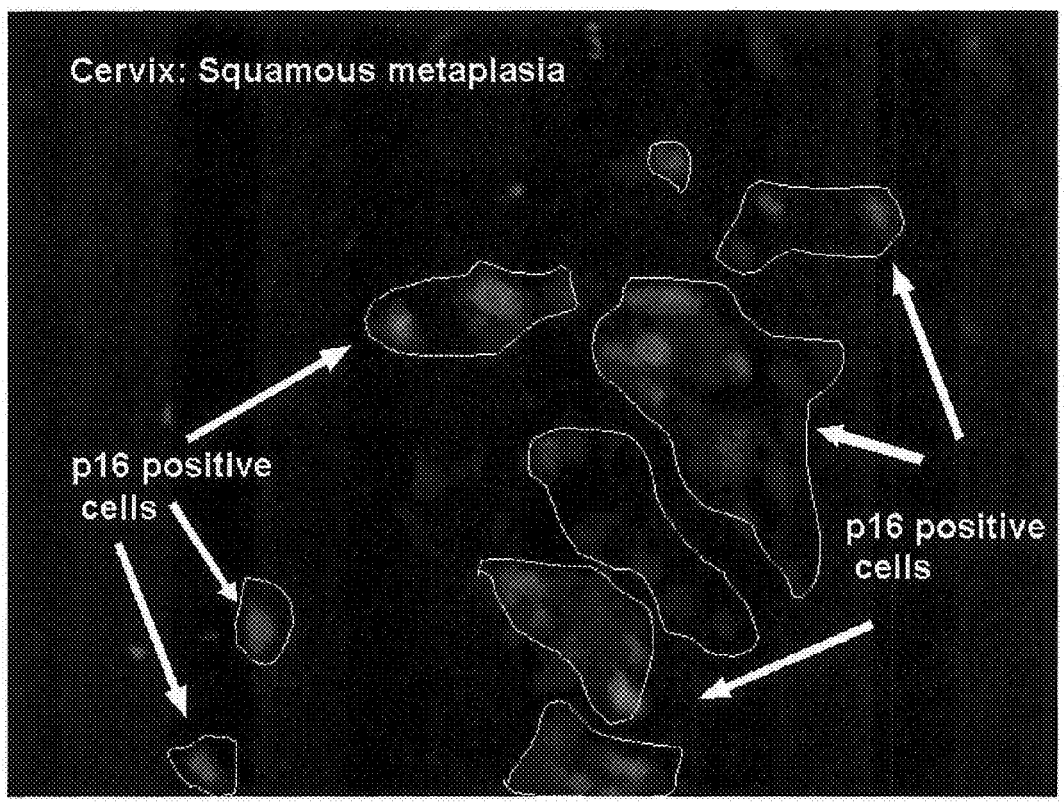
FIG. 4 is an example of fluorescent staining of a histological specimen of the cervix uteri.
Figure 5:
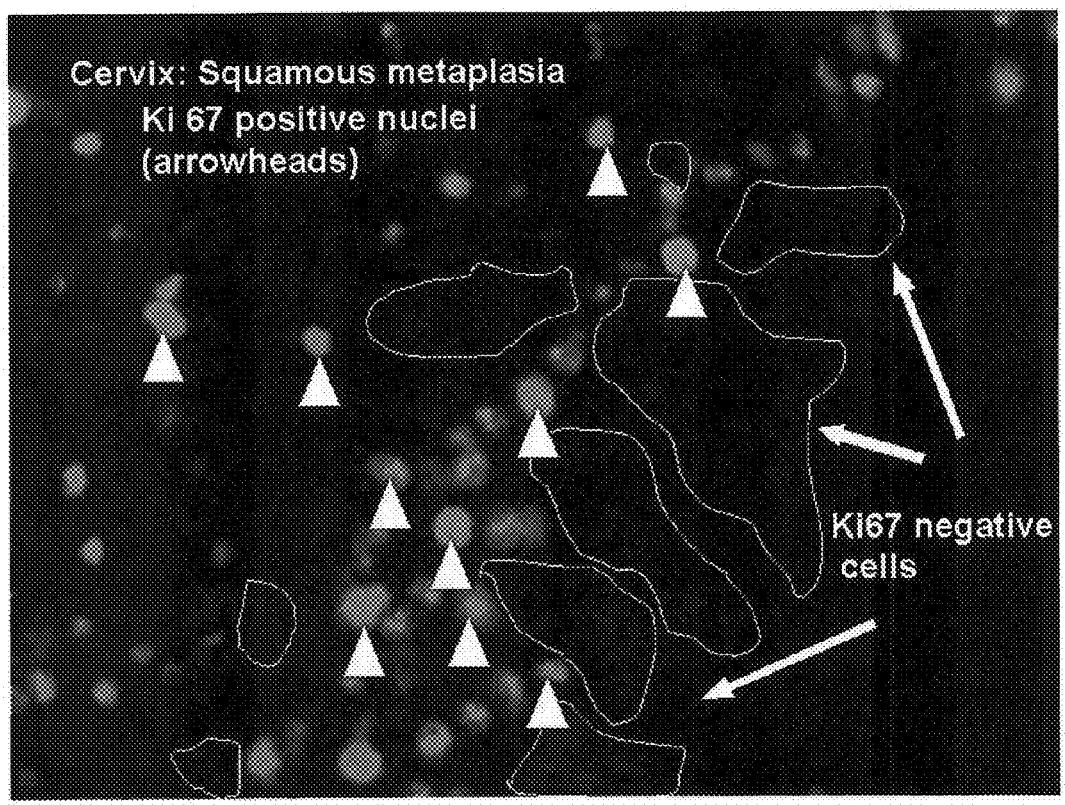
FIG. 5 is an example of fluorescent staining of a histological specimen of the cervix uteri.
Figure 6:
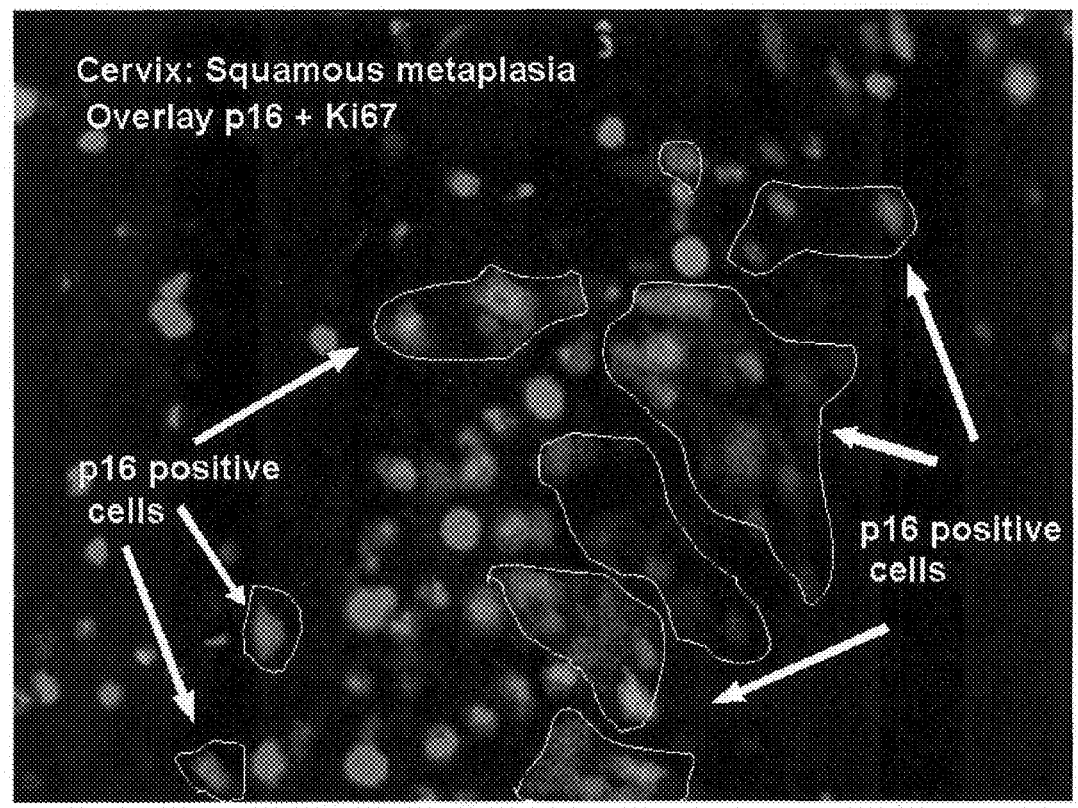
FIG. 6 is an example of fluorescent double staining of a histological specimen of the cervix uteri.

The present invention relates to a method for discrimination of neoplastic, pre-neoplastic and/or dysplastic lesions from non-dysplastic cells showing elevated levels of p16$^{INK4a}$, in biological samples in a histological or cytological testing procedure based on the detection of the presence or absence of cells expressing p16$^{INK4a}$ gene simultaneously with cell proliferation markers in said biological samples. Suitable markers for cell proliferation may be, e.g., Ki67, Ki-S2, Ki-S5, mcm5, or mcm2. In one embodiment of the invention, protein or mRNA of the markers for cell proliferation may serve as a marker for discrimination of metaplasias from early dysplastic or pre-neoplastic lesions in samples.

One aspect of the present invention is to provide a method for discriminating dysplastic cells over-expressing INK4a gene products from other cells expressing INK4a gene products at a detectable level in biological samples comprising determining in a cytological or histological testing procedure the co-expression of at least two marker molecules in at least one single cell, wherein at least one marker molecule is an expression product encoded by the INK4a gene and at least one further marker molecule is a cell proliferation marker, wherein the over-expression of at least one INK4a gene product and expression of at least one marker for active cell proliferation at an immuno-chemically detectable level within said single cell is indicative of the dysplastic state of the cell, and wherein the over-expression of at least one INK4a gene product and expression of at least one marker for senescence, terminal differentiation of cells, apoptosis, or cell cycle arrest at a detectable level within said single cell is indicative of the non-dysplastic state of the cell.

A second aspect of the present invention relates to a test kit for determination of dysplasias in samples according to the method disclosed herein.

During the experiments leading to the present invention, it was found that, under certain circumstances, non-dysplastic cells may show immunoreactivity for p16$^{INK4a}$. The inventors found that these cells exhibiting ordered control of cell proliferation in response to the elevated levels of the INK4a gene products are subject to growth arrest. Thus, these individual cells do not show immunoreactivity for markers of cell proliferation. In contrast, transformed cells over-expressing p16$^{INK4a}$ exhibit dysregulated control of cell proliferation, and do not respond to the elevated level of p16$^{INK4a}$ by cessation of proliferation. Thus, these dysplastic cell show simultaneous expression of p16$^{INK4a}$ with markers for cell proliferation. The inventors thus found that a simultaneous detection of p16$^{INK4a}$ with markers for cell proliferation may serve to discriminate dysplastic cells from arrested cells over-expressing p16$^{INK4a}$ such as, e.g., metaplastic cells.

The discovery that p16$^{INK4a}$ over-expressed in various dysplasias may also be detected in some other non-dysplastic cells led the inventors of the presented method to establish a technique for discrimination between non-dysplastic p16$^{INK4a}$ positive cells and dysplastic cells over-expressing p16$^{INK4a}$ based on the proliferation characteristics of the respective cells. Whereas in normal cells p16$^{INK4a}$ inhibits cdk4, and thus inhibits cell proliferation, this is not true for dysplastic cells. Thus, in dysplastic cells p16$^{INK4a}$ does not lead—despite it's uncommonly high expression level—to an inhibition of the cell proliferation.

The method disclosed herein is based on the fact that dysplastic cells may be discriminated from cells exhibiting normal cell proliferation by the simultaneous detection of an INK4a gene product such as, e.g., p16$^{INK4a}$, with a marker characteristic for cell proliferation.

The term marker, as well as marker molecules in general, shall be used herein to pertain to proliferation marker gene expression products as well as to INK4a gene expression products.

The denominations given throughout this text for genes may, in part, relate to the genes or proteins as they have been discovered from any organism. In the context of the present invention, this denomination shall confer to the respective homologue of the named markers in the organism which is particularly in question for a method as disclosed herein. In certain embodiments of the present invention, this organism is a mammal and, in one embodiment, may be a human being. Thus, in one embodiment of the present invention, the named markers shall be the human homologues of the respective denominated ones.

Generally throughout the text, the term "(cell) proliferation marker" or "marker for cell proliferation" in the various grammatical forms is used to denominate proteins as well as nucleic acid markers. In case the protein name of a marker such as e.g. "replication protein" is used herein, this use shall be understood metonymically and pertain as well to the protein as to the nucleic acid marker molecules encoding the particular protein A marker useful according to the present invention may be any molecule transcribed from a gene or any molecule translated from such a transcript. Thus, "gene product", as used in the context of the present invention, may comprise polynucleotides such as, e.g., DNA or RNA and polypeptides such as proteins, proteoglycans, peptides, etc. "Expression product(s)" as used in the context of the present invention shall comprise any transcript of a gene locus in forward or reverse direction including any reading frames and splicing variants. "Expression products" as used herein shall thus comprise any alternative products encoded by the nucleic acids of a particular gene locus.

INK4a encoded gene-products, as used in the context of the present invention, shall be any mRNA transcribed from the INK4a gene locus or any polypeptide translated from such an mRNA. In one embodiment of the invention, the expression products encoded by the INK4a gene may exhibit molecular weights of about 5 to 40 kDa or any value in between, and preferably of about 10 to 20 kDa or any value in between, and most preferably of about 14 to about 19 kDa or any value in between, respectively.

INK4a gene-products suitable for the method according to the present invention may comprise, e.g., gene-products such as, e.g., p16$^{INK4a}$ and p14ARF.

The term "(cell) proliferation marker" or "marker for cell proliferation", as used in the context of the present invention, shall comprise any marker molecule known in the art to be characteristic for the proliferation status of cells. The proliferation status may be, e.g., a status of actively proliferating cells, of retarded cell proliferation, of arrested cell proliferation, of senescent cells, of terminally differentiated cells, of apoptosis, etc. In one embodiment of the invention, the cell proliferation marker is a marker molecule characteristic for active cell proliferation. In another embodiment of the invention, the proliferation marker molecule may be a molecule characteristic for arrested, terminally differentiated, senescent, or apoptotic cells.

In certain embodiments, proliferation markers for use in the context of the present invention may comprise genes engaged in the DNA replication, such as e.g., proteins of the pre-initiation complex or of the replication fork. Such molecules may comprise, e.g., helicases, such as eucaryotic helicase or MCM proteins (MCM2, MCM3, MCM4, MOMS, MCM6, MCM7), protein TP as disclosed in WO0050451 and WO0217947 (also denominated HELAD1, Pomfil2, Unc-53), kinases or phosphatases engaged in the replication process such as, e.g., CDC6, CDC7 protein kinase, Dbf4, CDC14 protein phosphatase, CDC45 and MCM10. Furthermore, proliferation markers may comprise proteins engaged in the processive replication fork such as, e.g., PCNA or DNA polymerase delta, replication protein A (RPA), replication factor C (RFC), and FEN1.

In other embodiments, the proliferation markers may comprise molecules necessary for the maintenance of cell proliferation such as Ki67, Ki-S5, or Ki-S2. In this embodiment, proteins may be present, e.g., throughout the whole cell cycle. They are useful for performing a method according to the present invention provided they are characteristic of active cell proliferation and are not significantly expressed in arrested, terminally differentiated, apoptotic, or senescent states of cells. Ki67, Ki-S2, and Ki-S5 as used herein shall denominate the protein marker molecules detected by the respective antibodies as well as the nucleic acids encoding these antigens.

In another embodiment, the cell proliferation markers for use in a method according to the present invention may be a marker molecule characteristic of retarded or ceased cell proliferation such as, e.g., a senescence marker, a cell cycle arrest marker, a marker characteristic for terminally differentiated cells, or an apoptosis marker. Such molecules comprise, e.g., p21, p27, Caspases, BAD, CD95, fas-ligand, parp-proteins, etc.

Discrimination as used in the context of the present invention shall comprise an assessment whether a sample is to be classified in one or another way. In one embodiment of the invention, the discrimination pertains to the assessment of a tissue, or components thereof, being dysplastic or being not dysplastic. Thus, the discrimination as used herein is a judgement about the growth properties of cells in a biological sample.

In one embodiment of the present invention, the discrimination comprises the detection of expression of an INK4a gene product simultaneously with the detection of expression of a marker characteristic for active cell proliferation. In this case, cells co-expressing both marker molecules are to be classified as being dysplastic.

In another embodiment of the present invention, the discrimination comprises the detection of an INK4a gene product simultaneously with the detection of expression of a marker characteristic for arrested, ceased, or retarded cell proliferation. In this case, cells co-expressing both marker molecules are to be classified as being non-dysplastic.

In certain embodiments of the present invention, it will be useful to detect the presence or absence and/or the level of more than two marker molecules. In one embodiment, one INK4a gene expression product will be detected in concert with two or more markers for cell proliferation. This may be useful to enhance the identification of proliferation properties of the INK4a gene product-expressing cells in samples. Some proliferation markers are restricted to specific phases of the cell cycle or are present in low abundance in cells. Due to this fact, in some cases, the detection of proliferating cells expressing INK4a gene products may be improved by detection of two or more proliferation markers. In such cases, e.g., one proliferation being expressed during the whole proliferative cell cycle may be detected simultaneously by markers characteristic for specific cells cycle phases. For example, Ki67, Ki-S5, or Ki-S2 may be detected together with mcm5, mcm2, PCNA, rpA, rfC, etc. In other cases, e.g., proteins engaged in the DNA replication may be detected together with Ki67, Ki-S5, or Ki-S2. In yet another case, Ki67 may be detected together with Ki-S2. It must be understood that these examples are intended to exemplify combinatorial possibilities, and shall not be comprehensive, so that various other combinations of proliferation markers are likewise useful and suitable in the procedure of the method according to the present invention.

As the case may be, combination of two or more cell proliferation marker molecules may be applied in a method as disclosed herein. In another embodiment, two or more marker molecules detectable over larger stretches of the cell cycle or even over the whole cell cycle, or in an actively proliferating cell, may be detected in concert in a method as disclosed herein. A combination of more than one cell proliferation marker molecules may be useful generally for improving the sensitivity of the detection of the proliferation characteristics of cells.

In certain embodiments of the present invention, a combination may furthermore comprise other marker molecules such as senescence marker molecules, markers for arrested cells, markers for terminally differentiated cells, markers for apoptotic cells, markers for viral infection or for viral activity in cells, or cell cycle regulatory protein markers. In certain embodiments, in connection with dysplasias being associated with HPV infection, a detection of HPV associated marker molecules or markers for viral activity may be of use for a detection of a dysplasia. The methods useful for detection of HPV infection in samples are known to those of skill in the art. These methods may comprise methods employing probes specific for HPV agents or may employ nucleic acid amplification reactions. The detection of a viral infection may be carried out simultaneously or subsequently to the detection of the INK4a and proliferation marker molecules.

Dysplastic, as used in the context of the present invention, shall refer to dysplasias from mild to severe dysplasias and their precursory stages, as well as carcinoma such as carcinomas in situ or invasive carcinomas and disseminated tumor cells. Thus, dysplastic as used herein shall also comprise early and precursory stages of dysplasias and carcinomas.

Cells over-expressing INK4a gene products without being dysplastic (non-dysplastic as used herein) as mentioned herein may comprise, e.g., metaplastic cells, senescent cells, terminally differentiated cells, or cells that in certain stages of the cell cycle exhibit elevated levels of the INK4a gene products. In certain cells, elevated levels of INK4a gene products may even be effected as a response to external signals such as hormones, transmitters, etc. In one embodiment of the present invention, the non-dysplastic cells over-expressing INK4a gene products comprise, e.g., metaplastic cells, endometrial cells, etc.

The method for detection of the expression level of the INK4a encoded gene-products and/or the proliferation marker gene products according to the present invention is any method, which may (but need not) be, e.g., suited to detect even very small amounts of specific biological molecules in biological samples. The detection reaction according to the present invention is a detection either on the level of nucleic acids or on the level of polypeptides.

A marker molecule is said to be detectable as used in the context of the present invention, provided the marker may be detected in the course of suitable detection procedure such as, e.g., in situ hybridization, immuno-chemical staining, hybrid capture assay, etc. The level of expression of a marker molecule may be made detectable using suitable reporter reactions such as, e.g., a chromogenic or fluorescence based immuno-chemical staining or in-situ-hybridization procedure for microscopic or automated analysis. Suitable methods for enhancing the reporter signal known to those of skill in the art may be applied in the course of a method according to the present invention. Thus, the marker is said to be detectable in a case where the staining supersedes the respective background staining inherently obtained in the immuno-chemical staining procedure so as to produce significant staining results.

The marker molecules may be detected using reagents that specifically recognize these molecules. The detection reaction for the INK4a gene-products and/or the proliferation marker gene products may comprise one or more reactions with detecting agents either recognizing the initial marker molecules or recognizing the prior molecules used to recognize other molecules.

In certain embodiments of the present invention, two or more probes may be used for the detection of one single marker molecule. For example, two or more different binding agents (e.g., antibodies) or oligonucleotide probes directed against one single marker molecule (or, as the case may be, against different epitopes or different sequences) may be used in the course of the method as disclosed herein.

The detection of the different gene products may be performed in one reaction vessel or container or in different containers simultaneously or subsequently in time. Thus, the different gene products may be detected simultaneously in one cell co-expressing both products. Otherwise, cells co-expressing the gene products may be used for separated detection reaction (separated in space or in time) to detect each a single marker in the cells. In another embodiment, there might be cells expressing one or the other marker. The detection of the marker molecules in the different cells may also be performed simultaneously or separately in time and/or space.

The detection reaction further may comprise a reporter reaction indicating the presence or absence and/or the level of the marker molecule gene-products. The reporter reaction may be, for example, a reaction producing a coloured compound, a bioluminescence reaction, a fluorescence reaction, generally a radiation emitting reaction, etc.

In certain embodiments, different marker molecules may be recognized by agents that produce different reporter signals, so that the signals referring to marker molecules can be distinguished. In one preferred embodiment of the invention, the detection of the expression of the two or more INK4a gene-products and/or proliferation marker gene products is carried out simultaneously. In this case, the reporter reaction may employ, for example, different fluorescent labels for the different molecules detected.

However, within the context of the present invention, it must not necessarily be answered whether the one or the other proliferation marker or INK4a marker gene product is expressed in the cells. In certain embodiments, the question is whether any proliferation marker and/or INK4a gene product is expressed. In the course of the experiments, a procedure may be chosen that gives the same fluorescence signal as an indication of the presence of a proliferation marker. This procedure is suitable to improve sensitivity of the detection of the cell proliferation characteristics (different markers characteristic for active cell proliferation). As the case may be, the procedure may be applied so as to render one detectable signal for three, four, or even more marker molecules characteristic of cell proliferation. Analogously, the same may under certain circumstances be true for the INK4a gene expression products. It must be understood that different staining signals for different proliferation marker molecules may be desirable. The procedures may be applied to the necessities of the respective experiment.

In certain embodiments of the present invention, a combination of one or more (e.g., two different) INK4a gene products may be detected with a combination of one or more (e.g., a set of two, a set of three, a set of four, a set of five or a set of even more) markers for cells proliferation. In some cases, the detection of the marker molecules for cell proliferation may render only one reporter signal. In other cases, each single marker for cell proliferation may render a specific reporter signal or groups of marker molecules may render specific reporter signals.

Signals for the indication of the presence of immunoreactivity may be chromogenic signals produced by various methods known in the art. Alternatively, or even in combination, fluorescent signals may be used. Suitable reporter signals comprise fluorescent labels such as fluorescein, rhodamine, etc.

Applicable formats for the detection reaction according to the present invention may be blotting techniques, such as Western-Blot, Southern-blot, Northern-blot, and immunocytochemical, or immunohistochemical procedures. The blotting techniques are known to those of ordinary skill in the art, and may be performed as, for example electro-blots, semidry-blots, vacuum-blots or dot-blots. Immunocyto/histochemical staining procedures are known to those of skill in the art, and may comprise binding agent-mediated detection of polypeptides as well as in situ hybridisation techniques. Both different techniques may even be applied simultaneously. In certain embodiments, hybrid capture of nucleic acids may be used for the detection. Amplification reactions may also be applicable for the detection of e.g. nucleic acid molecules.

In one embodiment of the invention, the detection of the level of INK4a and/or proliferation marker gene-products is carried out by detection of the respective nucleic acids (e.g., mRNA) or fragments thereof present in the sample. The means for detection of nucleic acid molecules are known to those skilled in the art. The procedure for the detection of nucleic acids can be carried out by, for example, a binding reaction of the molecule to be detected to complementary nucleic acid probes, proteins with binding specificity for the nucleic acids, or any other entities specifically recognizing and binding to said nucleic acids. In one embodiment, in situ hybridisation of oligonucleotide probes to nucleic acids in a sample may be used for the detection of expression products or markers.

A probe, as used in the context of the present invention, may be any agent binding specifically to a molecule. In the case of nucleic acids, a probe may be an oligonucleotide hybridising to a particular sequence. In one embodiment, the probe may be, e.g., a primer. In the case of the detection of polypeptides or proteins, the probe as used herein may be, e.g., a binding agent such as an antibody. In certain embodiments of the present invention, the probes may be detectably labelled. The label may be selected from the group comprising a radioisotope, a bioluminescent compound, a chemiluminescent compound, a fluorescent compound, a metal chelate, or an enzyme. Probes may be applied in any detection procedure known in the art as, for example, in the course of an in situ hybridisation procedure, in the course of hybrid capture assays, in the course of immuno-chemical staining reaction, in the course of blotting techniques, etc.

This method may be performed as well in vitro as directly in situ for example, in the course of a detecting staining reaction. Another way of detecting the marker mRNAs in a sample performed in the method according to the present invention is an amplification reaction of nucleic acids, which can be carried out in a quantitative manner such as, for example, the polymerase chain reaction. In a preferred embodiment of the present invention, real time (RT) PCR may be used to quantify the level of marker mRNAs in samples of dysplasias or tumors (cells or tissue samples).

In another preferred embodiment of the invention, the detection of the level of INK4a and/or proliferation marker gene-products is carried out by determining the level of expression of a protein or fragments thereof. The determination of the marker gene-product on the protein level can, for example, be carried out in a reaction comprising a binding agent specific for the detection of the particular marker polypeptide.

The binding agents can be used in many different detection techniques including, for example, in western-blot, ELISA or immuno-precipitation. Generally, polypeptide binding agent based detection can be carried out as well in vitro as directly in situ as, for example, in the course of an immuno-chemical staining reaction. Any other method for determining the amount of particular polypeptides in biological samples can be used according to the present invention.

The immuno-cytochemical imaging procedures for use in the context of the present invention may comprise, e.g., the staining of cytological or histological preparations with chromogenic or fluorescent dyes. The staining may comprise, e.g., binding of the molecules to be detected by a first binding agent, which itself is detected by a secondary binding agent which may be labelled. The first binding agent may in certain embodiments be a nucleic acid or a protein binding agent (e.g. an antibody) and the secondary binding agent may be, e.g., a secondary antibody recognizing the first binding agent.

Any methods known in the art for performing staining of cytochemical or histochemical staining may be applied in the course of a method according to the present invention.

Binding agents as used in the context of the present invention for the detection of the level of INK4a polypeptides such as p16$^{INK4a}$ or p14ARF polypeptides and proliferation marker polypeptides such as, e.g., mcm5, mcm2, Ki67, Ki-S5, PCNA, or Ki-S2 polypeptides may comprise antibodies and antigen-binding fragments, bi-functional hybrid antibodies, peptidomimetics containing minimal antigen-binding epitopes, anti-cullines (anti-Caline™), etc.

An antibody or antigen-binding agent is said to react specifically if it reacts at a detectable level with a protein disclosed herein, and does not significantly react with other proteins. The antibodies according to the present invention may be monoclonal or polyclonal antibodies. As used herein, the term antibody or monoclonal antibody is meant to include intact molecules as well as antibody fragments. Moreover, antibodies of the present invention include chimeric, single chain, and humanized antibodies.

According to the present invention binding agents may be used isolated or in combination. By means of combination, it is possible to achieve a higher degree of sensitivity. The term antibody, preferably, relates to antibodies which consist essentially of pooled monoclonal antibodies with different epitopic specificities, as well as distinct monoclonal antibody preparations.

Monoclonal antibodies are made from antigen-containing fragments of the polypeptide of the invention using any of a variety of techniques known to those of ordinary skill in the art (see, e.g., Harlow and Lane, Antibodies: A Laboratory Manual, Cold Spring Harbor Laboratory, 1988). In one such technique, an immunogen comprising the antigenic polypeptide, or a synthetic part thereof, is initially injected into any of a wide variety of mammals (e.g., mice, rats, rabbits, sheep, and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Within the context of the present invention, it must not necessarily be answered whether one or the other proliferation marker is expressed in the cells. In certain embodiments, the main question may be whether any proliferation marker is expressed. In the course of the experiments, a procedure was chosen that gives the same fluorescence signal as an indication of the presence of a proliferation marker. This procedure is suitable to improve sensitivity of the detection of the cell proliferation characteristics. As the case may be, the procedure may be applied so as to render one detectable signal for three, four, or even more marker molecules characteristic for cell proliferation. Analogously, under certain circumstances, the same may be true for the INK4a gene expression products. it must be understood, that, as the case may be, different staining signals for different proliferation marker molecules may be desirable. The procedures may be applied to the necessities of the respective experiment.

The INK4a gene-products and/or proliferation marker gene products may, according to the present invention, be detected simultaneously. In this context, simultaneously according to the present invention shall mean either literally at the same instant or within the same testing procedure, whereby the single detection steps are temporarily consecutive.

The detection procedure according to the present invention may, furthermore, comprise a cytochemical staining procedure rendering a chromogenic or fluorescent staining of cells or cell compartments. Such staining procedures are known to those of skill in the art and may comprise, for example, staining for acidophilic or basophilic structures, of subcellular regions (e.g. the nucleus, the mitochondria, the golgi, the cytoplasm, etc.), of specific molecules (the chormosomes, of lipids, of glycoproteins, of polysaccharids, etc.) in the cytological specimens. Fluorescence dyes such as DAPI, Quinacrin, Chromomycin, etc. may be employed. Furthermore, chromogenic dyes such as Azan, Acridinorange, Hematoxylin, Eosin, Sudan-red, and Thiazin-stains (Toluidin-blue, Thionin) may be applied. In other embodiments, staining procedures such as Pap-staining, Giemsa-staining, Hematoxylin-Eosin staining, van-Gieson staining, Schiff-staining (using Schiff reagent), staining procedures employing precipitation of metals (such as, e.g., of silver in staining procedures employing Silver Nitrate), or insoluble stains such as, e.g., of Turnbulls-blue (or other insoluble metal cyanides), etc. may be used in the course of a method as disclosed herein. It must be understood, that the named dyes and staining methods shall be examples for the applicable methods, and that any other method known in the art may be applied to a method as disclosed herein.

The staining procedures may produce chromogenic stains for light microscopic inspection or fluorescent stains for inspection under fluorescence microscopic conditions. In another embodiment of the present invention, radiation emitting procedures, procedures employing substances impairing the transmission of radiation, or other contrast media for imaging of the cytological conditions in a sample (e.g., the generation of optical impression by means such as (micro-)autoradiographic or (micro-)radiographic picture generation) may be of use for a method according to the present invention.

All the staining and imaging procedures may be used for analysis not only in microscopic procedures, but also in automated analysis procedures such flow cytometry, automated microscopic (computerized or computer aided) analysis, or any other method for analysis of stained cytological specimens.

The analysis of the staining or imaging results of the different procedures may be performed in a single analysis step or in different subsequent steps. For example, the light microscopic inspection of a specimen may be performed before or after fluorescence microsopic inspection of the specimen. In fluorescence microscopy, the analysis of different stains with different excitation wavelengths may be analyzed simultaneously or subsequently. Other imaging methods may be employed simultaneously or subsequently to the named procedures.

There may be various circumstances, under which combinations of different staining methods will be suitable. For example, in cases where no satisfying cytological staining results may be achieved by immuno-chemical staining, the additional application of general cytological staining techniques may be suitable.

A sample according to the method of the present invention may comprise any sample comprising cells. Samples may comprise, e.g., secretions, smears, body fluids, and cell- or tissue-samples.

In one embodiment of the present invention, samples comprise cells of the anogenital tract, of the respiratory tract, or of the skin and its appendages. In certain embodiments, the cells may be cells of the uterine cervix, the vagina, the vulva, the penis, the anus, the rectum, the bronchic tree, the lung, the peritoneum, the peritoneal space, the naso-pharyngeal space, the oral cavity, or the skin. In certain embodiments of the present invention, the sample may be a histological sample, a biopsy, or a cytological sample such as, e.g., a smear, a swab, a wash, or a body fluid containing cells (sputum, a secretion, saliva, etc.). In certain embodiments of the present invention, the samples may comprise cells infected by papilloma virus. The samples may, in certain embodiments, comprise cervical smears, bronchioalveolar lavages, etc.

In certain special embodiments of the present invention, the sample may be prepared as a monolayer or thin layer preparation of a cytological specimen. The respective methods for preparation of monolayer or thin-layer preparation in cytology are known to those of skill in the art. In one embodiment, the preparation may comprise, e.g., the Thin-Prep technology. Other methods comprise conventional smears, or method employing suspensions of cells for preparation of the cytological specimens.

Preparation of a sample may comprise, e.g., obtaining a sample of a tissue, of a body fluid, or of cells from a patient. According to the present invention, preparation of the sample may also comprise several steps of further preparations of the sample, such as preparation of dissections, preparation of cell suspensions, spreading or applying the cells to be examined onto microscopic slides, preparation of tissue arrays, isolation of polypeptides or nucleic acids, preparation of solid phase fixed peptides or nucleic acids, or preparation of beads, membranes, or slides to which the molecules to be determined are coupled covalently or non-covalently.

In certain embodiments of the present invention, the method may be performed in an automated manner. The automation of the method may be achieved by automated staining and analysis of histological or cytological specimens on a solid surface by microscopic means. In another embodiment, the automation may comprise a flow-cytometric analysis of the staining of cells in solution.

The dysplastic lesions to which the method according to the present invention may be applied comprise any dysplastic lesions characterized by over-expression of INK4a gene products such as, e.g., p16$^{INK4a}$ or p14ARF. In certain embodiments, those lesions are dysplasias associated with infections by papilloma viruses such as, e.g., HPV. In one embodiment, the HPV may be a high risk HPV subtype such as HPV16, HPV18, HPV31, HPV 33, HPV35, HPV 39, HPV 45, HPV 51, HPV 52, HPV56, HPV 58, HPV 59, HPV 66, HPV 68, etc. In one embodiment, the dysplastic lesions that may be detected according to the present invention comprise anogenital lesions, lesions of the respiratory tract, lesions of the head and the neck, or lesions of the skin and its appendages. Such lesions may comprise dysplasias, e.g., of the anus or rectum, of the vulva, the vagina, the cervix or the penis, of the bronchic tree, the lung, the oral cavity, or the nasopharyngeal space.

Another aspect of the present invention is a testing kit for performing the method according to the present invention. The kit may be, for example, a diagnostic kit or a research kit.

A kit according to the present invention comprises at least an agent suitable for detecting the INK4a gene-products.

Thus a kit according to present invention may comprise:
  reagents for the detection of one or more INK4a gene-products;
  reagents for the detection of one or more proliferation marker gene-products;
  reagents and buffers commonly used for carrying out the detection reaction, such as buffers,
  reporters reactants (dyes, etc.), carrier substances, and others;
  INK4a gene product samples for carrying out a positive control reaction; and
  proliferation marker gene product samples for carrying out a positive control reaction.

The reagents for the detection of the marker gene-products may include any agent capable of binding to the marker gene-products. Such reagents may include proteins, polypeptides, nucleic acids, peptide nucleic acids, glycoproteins, proteoglycans, polysaccharides, or lipids.

The INK4a gene-product and proliferation marker gene product samples for carrying out a positive control may comprise, for example, nucleic acids in applicable form, such as solution or salt, peptides in applicable form, tissue section samples, or positive cells.

In a preferred embodiment of the invention, the detection of the marker gene-products is carried out on the level of polypeptides. In this embodiment, the binding agents may be, for example, antibodies specific for the marker gene-products or fragments thereof.

In another embodiment of the test kit, the detection of the marker gene-products is carried out on the nucleic acid level. In this embodiment of the invention, the reagent for the detection may be, for example, a nucleic acid probe or a primer reverse-complementary to said marker nucleic acids.

The present invention provides a method for the discrimination of neoplastic and/or dysplastic and pre-neoplastic lesions, identifiable by assessment of the over-expression of $p16^{INK4a}$, from other cells cells, which also detectably express $p16^{INK4a}$, in the course of histological and/or cytological testing procedures. The method is based on the detection of expressed gene-products of two or more INK4a gene products.

Thus the problem to be solved was to provide a method for discrimination between dysplastic cells and other cells lacking malignant growth potential. The method may be applied to any stage of dysplasias and may be especially useful in early stages, when cytological diagnostic methods based on the $p16^{INK4a}$ over-expression need further information for the identification of metaplastic cells.

Furthermore the present invention provides a kit for performing the method according to the present invention.

EXAMPLES

The following examples are given for the purpose of illustration only and are not intended to limit the scope of the invention disclosed herein. For the purpose of illustration, the methods disclosed herein are exemplified using histological preparations. The histological examples aid to judge whether the cells stained in one or the other way are to be classified as dysplastic or metaplastic. The methods may easily be transferred to cytological specimens by altering the protocol in appropriate manner. These alterations are known to those of ordinary skill in the art.

Example 1

Immunofluorescent Detection of the Over-Expression of $p16^{INK4a}$ and Ki67 in Samples of the Uterine Cervix (Double Staining)

Sections of formalin fixed, paraffin embedded tissue samples of the cervix uteri were immunofluorescent stained using antibodies specific for $p16^{INK4a}$ and Ki67.

The tissue sections were rehydrated through incubation in xylene and graded ethanol, and transferred to Aqua bidest. Antigen retrieval was carried out with 10 mM citrate buffer (pH 6.0) for $p16^{INK4a}$ and Ki67. Therefore, the slides were heated in a waterbath for 40 min at 95-98° C. The slides were cooled down to RT for 20 minutes, and transferred to washing buffer (50 mM Tris-HCl, 150 mM NaCl, 0.05% Tween 20/DakoCytomation: code no.: S3006).

To avoid non-specific binding of the secondary antibody (species: goat), the specimens were incubated with 10% goat serum for 30 min at RT.

The slides were then incubated with the primary antibodies, mouse anti-human $p16^{INK4a}$ antibody (3.48 μg/ml) and rabbit anti Ki67 (1:25) for 30 min at RT, after which the slides were rinsed with washing buffer and placed in a fresh buffer bath for 5 min. Excess buffer was tapped off, and each specimen was covered with 200 μl of the secondary reagent containing goat anti-mouse antibody, AlexaFluor® 488 conjugated and goat anti-rabbit antibody, and Alexa Fluo® 546 conjugated, and then incubated for 30 min at RT. Then slides were washed two times as before and directly mounted with a special mounting medium for fluorescence.

Microscopic examination of the slides revealed that cells immunoreactive with $p16^{INK4a}$ and also immunoreactive for Ki67 were only found in samples microscopically identified as samples of dysplastic lesions. Cells stained by the $p16^{INK4a}$ specific reaction originating from metaplasias were not stained by the reaction specific for Ki67. Microscopic inspection of the cell proliferation marker staining showed that metaplastic cells over-expressing $p16^{INK4a}$ were not immunoreactive with the antibodies directed against Ki67. Samples containing dysplastic tissue areas, in contrast, comprised cells that were immunoreactive with KI67 and with antibodies directed against $p16^{INK4a}$. So, in contrast to dysplasias in metaplasias, no cells were double stained using the Ki67 and $p16^{INK4a}$ specific antibodies.

FIGS. 1-6 show the staining results for a severe dysplasia of the cervix uteri and for a squamous metaplasia using antibodies directed against Ki67 and against $p16^{INK4a}$. Immunoreactivity for Ki67 rendered red fluorescence, immunoreactivity for $p16^{INK4a}$ rendered green fluorescence, and overlay of red and green fluorescence rendered yellow fluorescence. In the dysplastic specimen (FIGS. 1-3), many cells of the dysplasia showed nuclear positivity for Ki67, as well as positivity for $p16^{INK4a}$, and thus gave rise to yellow fluorescence (see FIG. 3). In contrast, in the metaplastic specimen (FIGS. 4-6), areas that positively expressed $p16^{INK4a}$ did not show any positive staining for Ki67, indicating lack of expression of the antigen in these areas. No double staining was observed in this specimen (FIG. 6) and thus, no cells in the specimen gave rise to yellow fluorescence.

These results show that the double staining of cells with reagents specific for Ki67 allows discrimination of $p16^{INK4a}$ over-expressing metaplasias from dysplasias.

Example 2

Detection of Cells Co-Expressing p14ARF and mcm2 in Samples of the Uterine Cervix by In Situ Hybridization Smears of the uterine cervix may be semi-quantitatively analysed for the mRNA level of $p16^{INK4a}$ and mcm2 in an in situ staining reaction. The staining reaction is performed as follows:

For rehydration, the spray-fixed smears are incubated in fresh 50% EtOH on a rocking device. The PEG film produced by the fixation procedure is removed by intensive rinsing. Then, the smears are rinsed in Aqua bidest. The smears are incubated with proteinese K (10 μg/ml in PBS) for 10 min at 37° C. Then, the slides are transferred to washing buffer (PBS/0.1% Tween20) and finally, the area containing the cells is surrounded with a lipid-pencil.

The hybridization mixture is prepared by mixing 50 μl of ready-to-use hybridization buffer (DAKO A/S, Glostrup, Denmark) with about 5-10 pmol of the probes. The probes are biotin- and Digoxygenin-labelled oligonucleotides of sequences complementary to the respective mRNAs.

The hybridization mixture is heated to 95° C. and afterwards, equilibrated to 37° C. After the boiling procedure, the smears are incubated with each 50 μl of the hybridization mixture for 4 hours at 42° C. The samples are washed in excess volumes of the wash buffers two times in 2×SSC at 37° C. for 15 min, and once in 1×SSC at 37° C. for 15 min. Then, the smears are rinsed two times at room temperature in 2×SSC. Following this washing procedure, the dissections are incubated for 30 min with blocking buffer (NEN, blocking buffer) at room temperature, followed by a 1 hour incubation with a 1:100 diluted (in blocking buffer, see above) Streptavidin-alkaline phosphatase and monoclonal mouse HRP-labeled anti-Digoxygenine antibodies (Molecular Probes). The smears are then washed 2 times in 1×PBS/0.1% Triton X-100 for 10 min at room temperature, followed by one wash step with 1×PBS, 50 mM $MgCl_2$ (pH 9.2) for 10 min at room temperature. Then the staining reaction is performed with ELF 97 phosphate (Molecular Probes) for 10 sec to 7 min at room temperature. Excess substrate is washed 3 times with 1×PBS/0.1% Triton X-100 for 10 min at room temperature. In a second staining step, the section is incubated with Tyramides-Alexa-Fluor 594 for 10 sec to 7 min. Excess substrate is washed 3 times with 1×PBS/0.1% Triton X-100 for 10 min at room temperature. Finally the smears are dipped in $H_2O_{dest.}$ and embedded with Fluorescence mounting medium (DakoCytomation). Then the stained dissections can be analysed by fluorescence microscopy.

Microscopic examination of the slides reveals that cells positive for expression of $p16^{INK4a}$ and mcm2 are only found in samples that are microscopically identified as samples of dysplastic lesions. Cells stained by the $p16^{INK4a}$ specific reaction that are identifiable as metaplasias are not stained by the reaction specific for mcm2. The microscopic inspection of the mRNA hybridization shows that metaplastic cells over-expressing $p16^{INK4a}$ do not significantly express mRNA of mcm2. Dysplastic cells, in contrast, are stained by in situ hybridization with probes specific for mcm2, and with probes directed against $p16^{INK4a}$. So, in contrast to dysplastic cells, in metaplastic cells, no double staining using the mcm2 and $p16^{INK4a}$ specific probes is observed.

These results show that the double staining of cells with reagents specific for mcm2 allows discrimination of $p16^{INK4a}$ over-expressing metaplasias from dysplasias.

Example 3

Immunofluorescent Detection of the Over-Expression of $p16^{INK4a}$ and Ki-S2 in Samples of the Uterine Cervix (Double Staining)

Merckofix® fixed cytological samples (conventional smears and liquid-based cytology (ThinPreps®)) of the cervix uteri are immunofluorescent stained using antibodies specific for $p16^{INK4a}$ and Ki-S2.

Conventional smears and liquid based cytological samples (ThinPreps®) are rehydrated in ethanol (50%) for 10 min and transferred in Aqua bidest. Antigen retrieval is carried out with 10 mM citrate buffer (pH 6.0) for $p16^{INK4a}$ and Ki67. Therefore, the slides are heated in a waterbath for 40 min at 95°-98° C. The slides are cooled down to RT for 20 minutes, transferred to washing buffer (50 mM Tris-HCl, 150 mM NaCl, 0.05% Tween 20/DakoCytomation: code no.: S3006), and finally, the samples are surrounded with a lipid-pencil.

To avoid non-specific binding of the secondary antibody (species: goat) the specimens are incubated with 10% goat serum for 30 min at RT.

The slides are then incubated with the primary antibodies, mouse anti-human $p16^{INK4a}$ antibody (clone E6H4) (3.48 µg/ml) and rabbit anti-Ki-S2 (1:25) for 30 min at RT, and then the slides are rinsed with washing buffer and placed in a fresh buffer bath for 5 min. Excess buffer is tapped off, and the specimen is covered with 200 µl of the secondary reagent containing goat anti-mouse antibody, AlexaFluor® 488 conjugated and goat anti rabbit antibody, and Alexa Fluor® 546 conjugated and then incubated for 30 min at RT. Then, slides are washed two times as before and directly mounted with a special mounting medium for fluorescence.

Microscopic examination of the slides reveals that cells immunoreactive with $p16^{INK4a}$ and Ki-S2 may be identified microscopically as dysplastic cells. Cells stained by the $p16^{INK4a}$ specific reaction, which are not stained by the reaction specific for Ki-S2, may be classified by an experienced pathologist as either being metaplastic or of endometrial origin. Microscopic inspection of the cell proliferation marker staining shows that metaplastic cells over-expressing $p16^{INK4a}$ are not immunoreactive with the antibodies directed against Ki-S2. Dysplastic cells, in contrast, are immunoreactive with Ki-S2 and with antibodies directed against $p16^{INK4a}$. So, in contrast to dysplastic cells, in metaplasias, no cells are double stained using the Ki-S2 and $p16^{INK4a}$ specific antibodies.

These results show that double staining of cells with reagents specific for Ki-S2 allows discrimination of $p16^{INK4a}$ over-expressing metaplastic cells from dysplastic cells.

Example 4

Immunofluorescent Detection of the Over-Expression of $p16^{INK4a}$, Ki67 and PCNA in Bronchioalveolar-Lavage Samples of Individuals with Diagnosed Small Cell Lung Cancer (Double Staining)

Cells contained in bronchioalveolar lavage specimens of patients are prepared according to ThinPrep technology. Merckofix®-fixed cytological samples of the lavages of patients diagnosed with small cell lung cancer are immunofluorescent stained using antibodies specific for $p16^{INK4a}$, Ki67, and PCNA.

In this experiment, a procedure is used that does not discriminate between staining originating from immunoreactivity against the two proliferation markers PCNA and Ki67. Within the context of the present invention, whether one or the other proliferation marker is expressed in the cells must not necessarily be answered. The main question is whether any proliferation marker is expressed. In the course of the experiments, a procedure is chosen that gives the same fluorescence signal as an indication of the presence of a proliferation marker. This procedure is suitable to improve sensitivity of the detection of the cell proliferation characteristics. As necessary, the procedure may be applied so as to render one detectable signal for three, four, or even more marker molecules characteristic of cell proliferation. Analogously, the same may under certain circumstances be true for the INK4a gene expression products. It must be understood that different staining signals for different proliferation marker molecules may be desirable. The procedures may be applied to the necessities of the respective experiment.

The tissue sections are rehydrated through incubation in xylene and graded ethanol, and then transferred to Aqua bidest. Conventional smears and liquid-based cytological samples (ThinPreps®) are rehydrated in ethanol (50%) for 10 min, and transferred in Aqua bidest. Antigen retrieval is carried out with 10 mM citrate buffer (pH 6.0) for $p16^{INK4a}$, Ki67, and PCNA. Therefore, the slides are heated in a waterbath for 40 min at 95-98° C. The slides are cooled down to RT for 20 minutes, transferred to washing buffer (50 mM Tris-HCl, 150 mM NaCl, 0.05% Tween 20/DakoCytomation: code no.: S3006), and finally, the samples are surrounded with a lipid-pencil.

To avoid non-specific binding of the secondary antibody (species: goat), the specimens are incubated with 10% goat serum for 30 min at RT.

The slides are then incubated with the primary antibodies, mouse anti-human p16$^{INK4a}$ antibody (3.48 µg/ml), rabbit anti-Ki67, and rabbit anti-PCNA (each 1:25) for 30 min at RT. The slides are then rinsed with washing buffer and placed in a fresh buffer bath for 5 min. Excess buffer is tapped off, and the specimen is covered with 200 µl of the secondary reagent (containing goat anti-mouse antibody, AlexaFluor® 488 conjugated and goat anti rabbit antibody and, Alexa Fluor® 546 conjugated) and then incubated for 30 min at RT. Then slides are washed two times as before and directly mounted with a special mounting medium for fluorescence.

Microscopic examination of the slides reveals that cells immunoreactive with p16$^{INK4a}$ and also with Ki67 or PCNA may be identified microscopically as cells of small cell lung cancer. Cells stained by the p16$^{INK4a}$ specific reaction, originating from metaplasias, are not stained by the reaction specific for Ki67 and PCNA. The microscopic inspection of the cell proliferation marker staining shows that metaplastic cells over-expressing p16$^{INK4a}$ are not immunoreactive with antibodies directed against Ki67 and PCNA. Samples containing dysplastic cells, in contrast, comprise cells, that are immunoreactive with Ki67/PCNA and with antibodies directed against p16$^{INK4a}$. So, in contrast to dysplasias, in metaplasias, no cells may be triple-stained using the Ki67, PCNA, and p16$^{INK4a}$ specific antibodies.

These results show that the triple staining of cells with reagents specific for Ki67/PCNA allows discrimination of p16$^{INK4a}$ over-expressing non-dysplastic cells from dysplasias.

Example 5

Flow Cytometric Detection of Dysplastic Cells by Simultaneous Detection of mcm5 mRNA, p14ARF Protein, and Ki67 Protein in Cells of Cervical Origin Cytological samples (Cell suspensions in PBS, pH 7.4) of the cervix uteri were fluorescent stained using antibodies specific for p14ARF and Ki-67 and oligoprobes for mcm-5 and evaluated by three-color fluorescent FACS analysis.

Cells were centrifuged, the supernatant decanted and fixed and permeabilized with 100 ml Permeafix (Ortho Diagnostic, Raitan, N.J., USA) for 1 hour at room temperature. Cells were washed in sterile PBS, pH 7.4, pelleted, and re-suspended in 100 ml Permeafix for 1 hour at room temperature.

Cells were washed in sterile PBS, pH 7.4, pelleted, and re-suspended in sterile PBS. They were incubated with PE-conjugated anti-p14ARF antibody and PE-Cy5-conjugated anti-Ki67 antibody for 1 h at +4° C. Cells were washed in sterile PBS, pH 7.4, pelleted, and re-suspended in 100 ml Permeafix for 30 min at room temperature. Cells were washed in sterile PBS, pelleted by centrifugation, and then washed again in 2× standard saline citrate (SSC). After centrifugation, the cell pellet was resuspended in hybridization solution (2×SSC, 30% formamide, sonicated salmon sperm, and yeast transfer DNA) containing 500 ng of 5-carboxy-fluorescein double end-labelled, mcm5-specific oligonucleotides probes. The intercellular hybridization was performed at 42° C. for 1 hour, followed by successive washes in 2×SSC, 0.5% Triton X-100, and 1×SSC, 0.5% Triton X-100 at 42° C. The cells were re-suspended for analysis in PBS, pH 8.3, and analyzed on a flow cytometer (FACScan, Becton Dickinson, IS). For each analysis, 30.000-100.000 gated events were collected. Data analysis was performed using CellQuest (Becton Dickinson, IS).

The flow cytometer analysis revealed that cells immunoreactive with p14ARF and Ki-67, and/or reactive for the oligoprobes of mcm5, could be identified only in samples of patients with dysplastic lesions of the cervix. Samples from women with no dysplastic lesions showed no concomitant staining of p14ARF with Ki67 or mcm5.

These results show that the double-or-triple staining of cells with reagents specific for Ki67 and/or mcm5 allows discrimination of p14ARF over-expressing non-dysplastic cells from p14ARF over-expressing dysplastic cells.

Example 6

Immunoenzymatic Detection of the Over-Expression of p16INK4a and Ki67 in Histological Samples of the Uterine Cervix (Sequential Double Staining)

Sections of formalin-fixed, paraffin-embedded tissue samples of the cervix uteri were immunoenzymatically double-stained using antibodies specific for p16INK4a and Ki67.

The tissue sections were rehydrated through incubation in xylene and graded ethanol, and transferred to Aqua bidest, Antigen retrieval was carried out with 10 mM citrate buffer (pH 6.0) for p16INK4a and Ki67. Therefore, the slides were heated in a waterbath for 40 min at 95-98° C. The slides were cooled down to RT for 20 minutes and transferred to washing buffer (DakoCytomation).

Endogenous peroxidase activities were blocked with 3% $H_2O_2$ (DakoCytomation) for 5 min at RT.

After washing the slides for 5 min at RT, they were incubated with the first primary antibody, mouse anti-human p16INK4a antibody (MTM) for 30 min at RT, and were then rinsed with washing buffer and placed in a fresh buffer bath for 5 min. Excess buffer was tapped off and each specimen was covered with 200 µl of the secondary reagent (EnVision goat anti mouse—Peroxidase/DakoCytomation), and incubated for 30 min at RT. Then slides were washed three times as before. For the chromogenic visualization, DAB (DakoCytomation) was used by incubating the slides with the substrate chromogen complex for 10 min at RT. The reaction was stopped in deionized water, and the slides placed in wash buffer.

After washing, the slides were incubated with the second primary antibody, rabbit anti-human Ki67 antibody (Dianova, clone Ab-3) for 30 min at RT, and were then rinsed with washing buffer and placed in a fresh buffer bath for 5 min. Excess buffer was tapped off, and each specimen was covered with 200 µl of the secondary reagent (goat anti rabbit—Alkaline Phosphatase labeled/DakoCytomation) and incubated for 30 min at RT. Then slides were washed three times as before. For the chromogenic visualization, FastRed (BioGenex) was used by incubating the slides with the substrate chromogen complex for 30 min at RT. The reaction was stopped in deionized water.

After counterstaining with hematoxylin (DakoCytomation) for 2 min at RT, the slides were incubated in running tap water for 10 min at RT, and then mounted with aqueous mounting medium (Aquatex/MERCK).

The microscopic examination of the slides revealed that cells immunoreactive with p16INK4a and Ki67 were found only in samples that were identified microscopically as samples of dysplastic lesions. Cells stained by the p16INK4a-specific reaction, originating from metaplasias, were not stained by the reaction specific for Ki67. Microscopic inspection of the cell proliferation marker staining showed that metaplastic cells over-expressing p16INK4a were not immunoreactive with antibodies directed against Ki67. Samples containing dysplastic tissue areas, in contrast, comprised cells that were immunoreactive with Ki67 and with antibodies directed against p16INK4a. So, in contrast to dysplasias, in metaplasias, no cells were double-stained using the Ki67 and p16INK4a specific antibodies.

Figure 7:
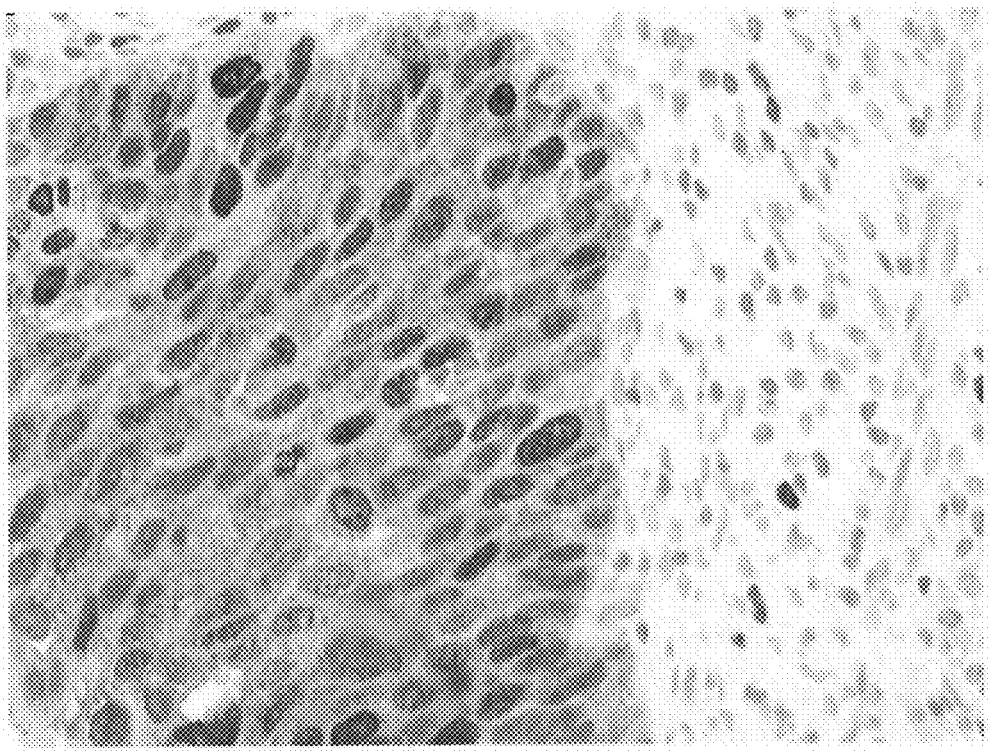
FIG. 7 is an example of chromogenic double staining of a histological specimen of the cervix uteri.

These results (FIG. 7) show that double staining of cells with reagents specific for Ki67 and p16INK4a also produces a specific double-staining pattern in chromogenic staining procedures.

Example 7

Immunoenzymatic Detection of the Over-Expression of $p16^{INK4a}$ and Ki67 in Cytological Samples of the Uterine Cervix (Sequential Double Staining)

Merckofix® fixed cytological samples (conventional smears and liquid-based cytology (ThinPreps®)) of the cervix uteri were immunoenzymatically double-stained using antibodies specific for $p16^{INK4a}$ and Ki67.

Conventional smears and liquid-based cytological samples were rehydrated in ethanol (50%) for 10 min at RT and transferred in Aqua bidest. Antigen retrieval was carried out with 10 mM citrate buffer (pH 6.0) for $p16^{INK4a}$ and Ki67. Therefore, the slides were heated in a waterbath for 40 min at 95-98° C. The slides were cooled down to RT for 20 minutes and transferred to washing buffer.

Endogenous peroxidase activities were blocked with 3% $H_2O_2$ for 5 min at RT.

After washing, the slides were incubated with the first primary antibody, mouse anti-human $p16^{INK4a}$ antibody, for 30 min at RT, and were then rinsed with washing buffer and placed in a fresh buffer bath for 5 min. Excess buffer was tapped off, and each specimen was covered with 200 μl of the secondary reagent (EnVision goat anti mouse—Peroxidase) and incubated for 30 min at RT. Then the slides were washed three times as before. For the chromogenic visualization, DAB (DakoCytomation) was used by incubating the slides with the substrate chromogen complex for 10 min at RT. The reaction was stopped in deionized water, and the slides placed in wash buffer.

After washing, the slides were incubated with the second primary antibody, rabbit anti-human Ki67 antibody (Dianova, clone Ab-3) for 30 min at RT, and were then rinsed with washing buffer and placed in a fresh buffer bath for 5 min. Excess buffer was tapped off, and each specimen was covered with 200 μl of the secondary reagent (goat anti rabbit—Alkaline Phosphatase labeled/DakoCytomation) and incubated for 30 min at RT. Then the slides were washed three times as before. For the chromogenic visualization, Fast Red (BioGenex) was used by incubating the slides with the substrate chromogen complex for 30 min at RT. The reaction was stopped in deionized water.

After counterstaining with hematoxylin (DakoCytomation) for 2 min at RT, the slides were incubated in running tap water for 10 min at RT, and then mounted with aqueous mounting medium (Aquatex/MERCK).

Microscopic examination of the slides revealed that cells immunoreactive with $p16^{INK4a}$ and Ki67 could be identified as dysplastic cells on the basis of their morphology. Cells stained by the $p16^{INK4a}$. specific reaction originating from metaplasias were not stained by the reaction specific for Ki67. The microscopic inspection of the cell proliferation marker staining showed that metaplastic cells over-expressing $p16^{INK4a}$ were not immunoreactive with the antibodies directed against Ki67. Dysplastic cells, in contrast, were immunoreactive with Ki67 and with antibodies directed against $p16^{INK4a}$. So, in contrast to metaplastic cells, in dysplastic cells, double-staining of single cells could be produced using the Ki67 and $p16^{INK4a}$ specific antibodies.

Figure 8:
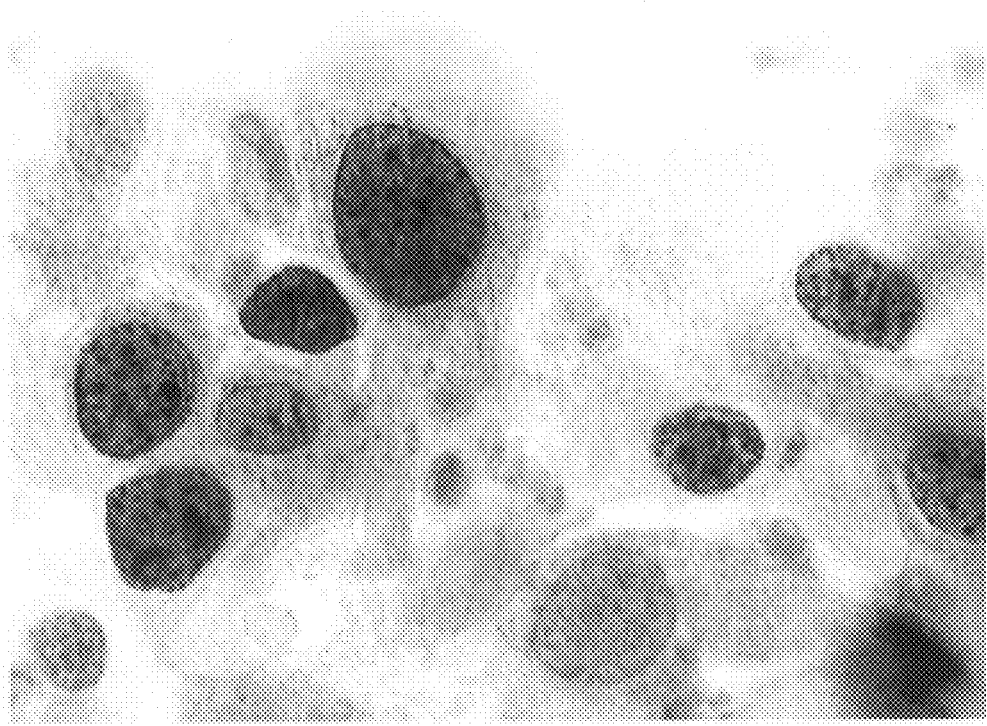
FIG. 8 is an example of chromogenic double staining of a cytological specimen of the cervix uteri.

These results (FIG. 8) show that the double staining of cells with reagents specific for Ki67 and p16INK4a also produces a specific double staining pattern in chromogenic staining procedures.

What is claimed:

1. A method of discriminating cervical dysplastic lesions from metaplastic lesions in a subject, the method comprising:
    (a) measuring an expression level of a high-risk HPV-associated nucleic acid in a sample collected from a cervical lesion in a subject;
    (b) measuring an expression level of at least one human protein marker selected from the group consisting of p14ARF and $p16^{INK4a}$ in the sample;
    (c) measuring an expression level of at least one human proliferation protein marker selected from a group consisting of MCM2, MCM5, CDC6, PCNA, and Ki67 in the sample;
    (d) determining that the lesion is dysplastic if there is a detectable level of the high-risk HPV-associated nucleic acid in the sample and there is at least one cell in the sample simultaneously expressing the protein marker of (b) and the proliferation protein marker of (c); and
    (e) determining that the lesion is metaplastic if there is a detectable level of the high-risk HPV-associated nucleic acid in the sample and if no cell in the sample co-expresses the protein marker of (b) and the proliferation protein marker of (c); thereby discriminating between dysplastic lesions from metaplastic lesions.

2. The method according to claim 1, wherein the protein marker of (b) is $P16^{INK4a}$.

3. The method according to claim 1, wherein the proliferation protein marker of (c) is MCM2 or MCM5.

* * * * *